US011944644B2

(12) United States Patent
Eshhar et al.

(10) Patent No.: US 11,944,644 B2
(45) Date of Patent: Apr. 2, 2024

(54) T-CELLS COMPRISING ANTI-CD38 AND ANTI-CD138 CHIMERIC ANTIGEN RECEPTORS AND USES THEREOF

(71) Applicants: THE MEDICAL RESEARCH INFRASTRUCTURE AND HEALTH SERVICES FUND OF THE TEL AVIV MEDICAL CENTER, Tel Aviv (IL); YEDA RESEARCH AND DEVELOPMENT CO. LTD., Rehovot (IL)

(72) Inventors: Zelig Eshhar, Tel Yitzhak (IL); Tova Waks, Petach Tikva (IL); Anat Globerson Levin, Tel Aviv (IL); Moran Rawet Slobodkin, Tel Aviv (IL)

(73) Assignees: THE MEDICAL RESEARCH INFRASTRUCTURE AND HEALTH SERVICES FUND OF THE TEL AVIV MEDICAL CENTER, Tel Aviv (IL); YEDA RESEARCH AND DEVELOPMENT CO. LTD, Rehovot (IL)

(*) Notice: Subject to any disclaimer, the term of this patent is extended or adjusted under 35 U.S.C. 154(b) by 375 days.

(21) Appl. No.: 16/769,111

(22) PCT Filed: Dec. 4, 2018

(86) PCT No.: PCT/IL2018/051325
§ 371 (c)(1),
(2) Date: Jun. 2, 2020

(87) PCT Pub. No.: WO2019/111249
PCT Pub. Date: Jun. 13, 2019

(65) Prior Publication Data
US 2020/0384024 A1    Dec. 10, 2020

Related U.S. Application Data

(60) Provisional application No. 62/667,638, filed on May 7, 2018, provisional application No. 62/594,577, filed on Dec. 5, 2017.

(51) Int. Cl.
| | |
|---|---|
| A61K 39/00 | (2006.01) |
| A61K 35/17 | (2015.01) |
| A61K 39/395 | (2006.01) |
| A61P 35/00 | (2006.01) |
| C07K 16/28 | (2006.01) |
| C07K 16/30 | (2006.01) |
| C12N 5/0783 | (2010.01) |

(Continued)

(52) U.S. Cl.
CPC ...... *A61K 35/17* (2013.01); *A61K 39/001126* (2018.08); *A61K 39/001129* (2018.08); *A61K 39/3955* (2013.01); *A61K 39/39558* (2013.01); *A61K 39/4631* (2023.05); *A61P 35/00* (2018.01); *C07K 16/28* (2013.01); *C07K 16/2896* (2013.01); *C07K 16/3061* (2013.01); *C12N 5/0636* (2013.01); *C12N 5/10* (2013.01); *C12N 15/63* (2013.01); *A61K 2039/505* (2013.01); *C07K 16/30* (2013.01); *C07K 2317/24* (2013.01); *C07K 2317/31* (2013.01); *C07K 2317/56* (2013.01); *C07K 2317/569* (2013.01); *C07K 2317/76* (2013.01); *C07K 2319/03* (2013.01)

(58) Field of Classification Search
CPC .......... A61K 39/395; A61K 39/001126; A61K 39/001129; A61K 2039/505; A61K 39/3955; A61K 39/39558; C07K 16/2896; C07K 16/30; C07K 2319/00; C07K 2319/31; C07K 2317/31; C07K 2317/56; C07K 2317/565; C07K 2317/569; C07K 2317/24
See application file for complete search history.

(56) References Cited

U.S. PATENT DOCUMENTS

| | | | |
|---|---|---|---|
| 7,829,673 B2 | 11/2010 | De Weers | |
| 8,614,301 B2 | 12/2013 | Arber | |
| 9,221,914 B2 | 12/2015 | Kraus | |
| 9,603,927 B2 | 3/2017 | Doshi | |
| 2014/0099309 A1 | 4/2014 | Powell, Jr. | |
| 2015/0342993 A1 | 12/2015 | Kloss | |
| 2018/0305433 A1* | 10/2018 | Pulé | C07K 16/00 |

FOREIGN PATENT DOCUMENTS

| | | |
|---|---|---|
| CN | 107326014 A | 11/2017 |
| IL | 231919 A | 2/2020 |

(Continued)

OTHER PUBLICATIONS

Bhattacharya et al. Impact of genetic variation on three dimensional structure and function of proteins. PLoS ONE 12(3): e0171355, 2017.*

(Continued)

*Primary Examiner* — Bridget E Bunner
(74) *Attorney, Agent, or Firm* — Dorsey & Whitney LLP

(57) ABSTRACT

The present invention provides T-cells expressing at least two different chimeric antigen receptors, wherein one of the CARs binds specifically to CD138 and another CAR binds specifically to CD38. In particular, the present invention provides T-cells expressing two different CARs, when one CAR comprises anti-CD138 sc Fv and the second CAR anti-CD138 sc Fv. Further, the invention provides a pharmaceutical composition comprising these dual CAR T-cells and their use in treatment of cancer, in particular multiple myeloma, and methods for preparation of these cells.

19 Claims, 5 Drawing Sheets
Specification includes a Sequence Listing.

(51) Int. Cl.
      C12N 5/10       (2006.01)
      C12N 15/63      (2006.01)

(56) References Cited

FOREIGN PATENT DOCUMENTS

| WO | 2006099875 A1 | 9/2006 |
| WO | 2014055668 A1 | 4/2014 |
| WO | 2014138704 A1 | 9/2014 |
| WO | 2014152177 A1 | 9/2014 |
| WO | 2015142314 A1 | 9/2015 |
| WO | 2015142675 A2 | 9/2015 |
| WO | WO-2016130598 A1 * | 8/2016 |
| WO | 2016210293 A1 | 12/2016 |
| WO | 2016210447 A1 | 12/2016 |
| WO | 2017025323 A1 | 2/2017 |
| WO | 2017027291 A1 | 2/2017 |
| WO | 2017040945 A1 | 3/2017 |
| WO | 2017149515 A1 | 9/2017 |
| WO | 2018144535 A1 | 8/2018 |
| WO | 2019111250 A1 | 6/2019 |

OTHER PUBLICATIONS

Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Brorson et al. Mutational analysis of avidity and fine specificity of anti-levan antibodies. J Immunol 163: 6694-6701, 1999.*
Brummell et al. Probing the combining site of an anti-carbohydrate antibody by saturation-mutagenesis: role of the heavy-chain CDR3 residues. Biochem 32(4): 1180-1187, 1993.*
Burks et al. In vitro scanning saturation mutagenesis of an antibody binding pocket. Proc Natl Acad Sci USA 94: 412-417, 1997.*
Cassett et al. A peptide mimetic of an anti-CD4 monoclonal antibody by rationale design. Biochem Biophys Res Comm 307: 198-205, 2003.*
Chen et al. J Mol Biol 293: 865-881, 1999.*
Colman Research in Immunol. 145:33-36, 1994.*
De Pascalis et al. Grafting and "abbreviated" complementarity-determining regions containing specificity-determining residues essential for ligand contact to engineer a less immunogenic humanized monoclonal antibody. J Immunol 169: 3076-3084, 2002.*
Doerks et al. Protein annotation: detective work for function prediction. Trends in Genetics 14:248-250, 1998.*
Fenton et al. Rheostat positions: a new classification of protein positions relevant to pharmacogenomics. Medicinal Chem Res 29: 1133-1146, 2020.*
Guo et al. Protein tolerance to random amino acid change. Proc Natl Acad Sci USA 101(25): 9205-9210, 2004.*
Holm et al. Functional mapping and single chain construction of the anti-cytokeratin 8 monoclonal antibody TS1. Mol Immunol 44: 1075-1084, 2007.*
Jang et al. The structural basis for DNA binding by an anti-DNA autobody. Mol Immunol 35: 1207-1217, 1998.*
Kobayashi et al. Tryptophan H33 plays an important role in pyrimidine (6-4) pyrimidone photoproduct binding by a high-affinity antibody. Protein Engineering 12(10): 879-884, 1999.*
MacCallum et al. Antibody-antigen interactions: contact analysis and binding site topography. J Mol Biol 262: 732-745, 1996.*
Ngo et al. "Computational complexity, protein structure prediction, and the Levinthal paradox" in The Protein Folding Problem and Tertiary Structure Prediction, pp. 492-495, 1994.*
Paul, William E., Fundamental Immunology, 3rd Edition, Raven Press, New York, Chapt. 8, pp. 292-295 (1993).*
Rudikoff et al. Single amino acid substitution altering antigen-binding specificity. Proc Natl Acad Sci USA 79: 1979-1983, 1982.*
Sela-Culang et al. The structural basis of antibody-antigen recognition. Front Immunol 4: 302, 2013 (13 total pages).*
Skolnick et al. From genes to protein structure and function: novel applications of computational approaches in the genomic era. Trends Biotechnol 18(1):34-39 2000.*
Smith et al. The challenges of genome sequence annotation or "the devil is in the details". Nature Biotechnol 15: 1222-1223, 1997.*
Tokuriki et al. Stability effects of mutations and protein evolvability. Curr Opin Structural Biol 19: 596-604, 2009.*
Vajdos et al. Comprehensive functional maps of the antigen-binding site of an anti-ErbB2 antibody obtained with shotgun scanning mutagenesis. J Mol Biol 320: 415-428, 2002.*
Vasudevan et al. A single amino acid change in the binding pocket alters specificity of an anti-integrin antibody AP7.4 as revealed by its crystal structure. Blood Cells Mol Diseases 32: 176-181, 2004.*
Wells, J.A. Additivity of mutational effects in proteins. Biochemistry 29(37): 8509-8517, 1990.*
Wu et al. Humanization of a murine monoclonal antibody by simultaneous optimization of framework and CDR residues. J Mol Biol 294: 151-162, 1999.*
Zhang et al. Comprehensize optimization of a single-chain variable domain antibody fragment as a targeting ligand for a cytotoxic nanoparticle. mAbs 7(1): 42-52, 2015.*
Newick et al., (2016) Chimeric antigen receptor T-cell therapy for solid tumors. Molecular Therapy—Oncolytics 3: 16006; 7 pages.
Tchou et al., (2017) Safety and Efficacy of Intratumoral Injections of Chimeric Antigen Receptor (CAR) T Cells in Metastatic Breast Cancer. Cancer Immunol Res 5(12): 1152-1161.
Ali et al., (2016) T cells expressing an anti-B-cell maturation antigen chimeric antigen receptor cause remissions of multiple myeloma. Blood 128(13): 1688-700.
Atanackovic et al., (2016) Chimeric Antigen Receptor (CAR) therapy for multiple myeloma. Br J Haematol 172(5): 685-698.
Baldwin et al., (2012) Ten-year relative survival for epithelial ovarian cancer. Obstet Gynecol 120(3): 612-618.
Bhattacharyya et al., (2012) T-cell immunotherapy with a chimeric receptor against CD38 is effective in eradicating chemotherapy-resistant B-cell lymphoma cells overexpressing survivin induced by BMI-1. Blood Cancer J 2(6): e75; 3 pages.
Campana et al., (2000) CD38 in hematopoiesis. Chem Immunol 75: 169-188.
Carpenter et al., (2013) B-cell maturation antigen is a promising target for adoptive T-cell therapy of multiple myeloma. Clin Cancer Res 19(8): 2048-2060.
Chen et al., (2018) A compound chimeric antigen receptor strategy for targeting multiple myeloma. Leukemia 32(2): 402-412.
Cohen (2018) CAR T Cells and Other Cellular Therapies for Multiple Myeloma: 2018 Update. Am Soc Clin Oncol Educ Book 38: e6-e15.
Cohen et al., (2019) B cell maturation antigen-specific CAR T cells are clinically active in multiple myeloma. J Clin Invest 129(6): 2210-2221.
Danhof et al., (2018) CARs and other T cell therapies for MM: The clinical experience. Best Pract Res Clin Haematol. Author manuscript; available in PMC Jul. 1, 2019. Published in final edited form as: Best Pract Res Clin Haematol. Jun. 2018; 31(2): 147-157.
de Felipe et al., (1999) Use of the 2A sequence from foot-and-mouth disease virus in the generation of retroviral vectors for gene therapy. Gene Ther 6(2): 198-208.
Deaglio et al., (2001) Human CD38: a (r)evolutionary story of enzymes and receptors. Leuk Res 25(1): 1-12.
Deshet-Unger et al., "Targeting Ovarian Cancer Using Double Car T Cells". Poster Presented at EACR-AACR-ISCR Conference: The Cutting Edge of Contemporary Cancer Research. Oct. 9-11, 2018, Jerusalem, Israel. 1 page.
Deterre et al., (2000) CD38 in T- and B-cell functions. Chem Immunol 75: 146-168.
Drent et al., (2016) Pre-clinical evaluation of CD38 chimeric antigen receptor engineered T cells for the treatment of multiple myeloma. Haematologica 101(5): 616-625.
Eshhar et al., (2014) The emergence of T-bodies/CAR T cells. Cancer J 20(2): 123-126.

(56) References Cited

OTHER PUBLICATIONS

Fedorov et al., (2014) Novel approaches to enhance the specificity and safety of engineered T cells. Cancer J 20(2): 160-165.

Fonseca and Monge (2013) Myeloma: classification and risk assessment. Semin Oncol 40(5): 554-566.

Gauthier and Yakoub-Agha (2017) Chimeric antigen-receptor T-cell therapy for hematological malignancies and solid tumors: Clinical data to date, current limitations and perspectives. Curr Res Transl Med 65(3): 93-102.

Globerson-Levin et al., (2014) Elimination of progressive mammary cancer by repeated administrations of chimeric antigen receptor-modified T cells. Mol Ther 22(5): 1029-1038.

Globerson Levin; "CAR T Cells Promising Immunotherapy for Cancer; From Basic Research to Cancer Treatment". Presented at the 2nd Annual Next Gen Immuno Oncology Congress 2018, London. 31 pages.

Goff et al., (2000) Ovarian carcinoma diagnosis: Results of a National Ovarian Cancer Survey. Cancer 89(10): 2068-2075.

Gross and Eshhar (1992) Endowing T cells with antibody specificity using chimeric T cell receptors. FASEB J 6(15): 3370-3378.

Gross and Eshhar (2016) Therapeutic Potential of T Cell Chimeric Antigen Receptors (CARs) in Cancer Treatment: Counteracting Off-Tumor Toxicities for Safe CAR T Cell Therapy. Annu Rev Pharmacol Toxicol 56: 59-83.

Hasegawa and Hosen (2019) Chimeric antigen receptor T cell therapy for multiple myeloma. Inflamm Regen 39: 10; 5 pages.

Jayson et al., (2014) Ovarian cancer. Lancet 384(9951): 1376-1388.

Kloss et al., (2013) Combinatorial antigen recognition with balanced signaling promotes selective tumor eradication by engineered T cells. Nat Biotechnol 31(1): 71-75.

Lee et al., (2018) An APRIL-based chimeric antigen receptor for dual targeting of BCMA and TACI in multiple myeloma. Blood 131(7): 746-758.

Liegel et al., (2018) Cellular immunotherapy as a therapeutic approach in multiple myeloma. Accepted manuscript; published as: Expert Rev Hematol 11(7): 525-536; 40 pages.

Lokhorst et al., (2015) Targeting CD38 with Daratumumab Monotherapy in Multiple Myeloma. N Engl J Med 373(13): 1207-1219.

Maliar et al., (2012) Redirected T cells that target pancreatic adenocarcinoma antigens eliminate tumors and metastases in mice. Gastroenterology 143(5): 1375-1384.

Perez-Amill et al., (2018) CAR-T Cell Therapy: A Door Is Open to Find Innumerable Possibilities of Treatments for Cancer Patients. CAR-T Hücre Tedavisi: Kanser Hastalarına Sayısız Tedavi Olanağı Bulunması için Kapı Aralandı. Turk J Haematol 35(4): 217-228.

Raje et al., (2019) Anti-BCMA CAR T-Cell Therapy bb2121 in Relapsed or Refractory Multiple Myeloma. N Engl J Med 380(18): 1726-1737.

Richardson et al., (2011) Monoclonal antibodies in the treatment of multiple myeloma. Br J Haematol 154(6): 745-754.

Rousseau et al., (2012) Dosimetry results suggest feasibility of radioimmunotherapy using anti-CD138 (B-B4) antibody in multiple myeloma patients. Tumour Biol 33(3): 679-688.

Ruella et al., (2016) Dual CD19 and CD123 targeting prevents antigen-loss relapses after CD19-directed Immunotherapies. J Clin Invest 126(10): 3814-3826.

Shubinsky and Schlesinger (1997) The CD38 lymphocyte differentiation marker: new insight into its ectoenzymatic activity and its role as a signal transducer. Immunity 7(3): 315-324.

Smith et al., (2019) GPRC5D is a target for the immunotherapy of multiple myeloma with rationally designed CAR T cells. Sci Transl Med 11(485): eaau7746; 15 pages.

Sun et al., (2019) Safety and efficacy of targeting CD138 with a chimeric antigen receptor for the treatment of multiple myeloma. Oncotarget 10(24): 2369-2383.

Tenca et al., (2003) Death of T cell precursors in the human thymus: a role for CD38. Int Immunol 15(9): 1105-1116.

Touzeau and Moreau (2017) Daratumumab for the treatment of multiple myeloma. Accepted manuscript; published as: Expert Opin Biol Ther 17(7): 887-893. 18 pages.

Yang and Yi (2011) Therapeutic monoclonal antibodies for multiple myeloma: an update and future perspectives. Am J Blood Res 1(1): 22-33.

Database clinical trials [online] NIH. Lung-Ji Chang; Multi-CAR T Cell Therapy in the Treatment of Multiple Myeloma. ClinicalTrials. gov Identifier: NCT03271632. <URL: https://clinicaltrials.gov/ct2/show/study/NCT03271632> Feb. 26, 2018.

Database clinical trials [online] NIH. Zhujiang Hospital; CAR-T Cells Therapy in Relapsed/Refractory Multiple Myeloma (MM). ClinicalTrials.gov Identifier: NCT03473496. <URL: https://clinicaltrials.gov/ct2/show/NCT03473496> Apr. 18, 2018.

IMGT/2Dstructure-DB card for INN 9128. Retrieved from: https://web.archive.org/web/20150425031816/http://www.imgt.org/3Dstructure-DB/cgi/details.cgi?pdbcode=9128 [dated Apr. 25, 2015], on Oct. 29, 2020. 4 pages.

UniProtKB/Swiss-Prot: P18827.2; RecName: Full=Syndecan-1; Short=SYND1; AltName: CD_antigen=CD138; Flags: Precursor. Dated Apr. 14, 2009 (Apr. 14, 2009); retrieved from: https://www.ncbi.nlm.nih.gov/protein/P18827.2 on Oct. 29, 2020. 4 pages.

Sherbenou et al., (2015) The development of potential antibody-based therapies for myeloma. Blood Rev. Author manuscript; available in PMC Jun. 26, 2015. Published in final edited form as: Blood Rev. Mar. 2015; 29(2): 81-91.

Stevenson (2006) CD38 as a therapeutic target. Mol Med 12(11-12): 345-346.

Wilkie et al., (2012) Dual targeting of ErbB2 and MUC1 in breast cancer using chimeric antigen receptors engineered to provide complementary signaling. J Clin Immunol 32(5): 1059-1070.

Can-Can et al., (2021) Off-target effect and optimization of CAR-T cell therapy in solid tumors. Chinese Journal of Immunology 37: 2754-2758. Abstract.

Hao He and Wang Zhiyu (2017) Off-target effects of CAR-T cells in tumor therapy and prevention strategies. Chinese Journal of Cancer Biotherapy 24: 317-322. Translated abstract.

Lanitis et al., (2013) Chimeric antigen receptor T Cells with dissociated signaling domains exhibit focused antitumor activity with reduced potential for toxicity in vivo. Cancer Immunol Res 1(1): 43-53.

Ayed et al., (2015) Immunotherapy for multiple myeloma: Current status and future directions. Critical Reviews in Oncology/Hematology 96(3): 399-412.

Chang et al., (2015) Abstract 3149: Chimeric antigen receptor-modified T cells against several target antigens in multiple myeloma. Proceedings: AACR 106th Annual Meeting 2015; Apr. 18-22, 2015; Philadelphia, PA. Aug. 1, 2015 (Aug. 1, 2015). Retrieved from the Internet: URL: https://cancerres.aacrjournals.org/content/75/15_Supplement/3149.

Globerson et al., (2020) Treatment of Multiple Myeloma Using Chimeric Antigen Receptor T Cells with Dual Specificity. Cancer Immunol Res 8(12): 1485-1495.

Guo et al., (2016) CD138-directed adoptive immunotherapy of chimeric antigen receptor (CAR)-modified T cells for multiple myeloma. Journal of Cellular Immunotherapy 2(1): 28-35.

Lanitis et al., (2012) Primary human ovarian epithelial cancer cells broadly express HER2 at immunologically-detectable levels. PLoS One 7(11): e49829; 12 pages.

Anitis et al., (2013) Chimeric antigen receptor T Cells with dissociated signaling domains exhibit focused antitumor activity with reduced potential for toxicity in vivo. Cancer Immunol Res. Author manuscript; available in PMC Jul. 1, 2014. Published in final edited form as: Cancer Immunol Res. Jul. 1, 2013; 1(1): 43-53.

Orecchia et al., (2013) A novel human anti-syndecan-1 antibody inhibits vascular maturation and tumour growth in melanoma. Eur J Cancer 49(8): 2022-2033.

Salnikov et al., (2013) Antibody targeting of CD24 efficiently retards growth and influences cytokine milieu in experimental carcinomas. Br J Cancer 108(7): 1449-1459.

Sun et al., (2014) Construction and evaluation of a novel humanized HER2-specific chimeric receptor. Breast Cancer Res 16(3): R61; 10 pages.

Zhu et al., (2017) CAR-T cell therapy in ovarian cancer: from the bench to the bedside. Oncotarget 8(38): 64607-64621.

(56) References Cited

OTHER PUBLICATIONS

Fesnak et al., (2016) Engineered T cells: the promise and challenges of cancer immunotherapy. Nat Rev Cancer 16(9): 566-581.
Finlay and Almagro (2012) Natural and man-made V-gene repertoires for antibody discovery. Front Immunol 3: 342, pp. 1-18. doi: 10.3389/fimmu.2012.00342.
Geldres et al., (2016) Chimeric antigen receptor-redirected T cells return to the bench. Semin Immunol 28(1): 3-9.
Hanada and Restifo (2013) Double or nothing on cancer immunotherapy. Nature Biotechnology 31: 33-34.
Sadelain et al., (2013) The basic principles of chimeric antigen receptor design. Cancer Discov 3(4): 388-398.

* cited by examiner

CAR-CD138                    Dual CAR

SEQUENCE LISTING

```
<160> NUMBER OF SEQ ID NOS: 39

<210> SEQ ID NO 1
<211> LENGTH: 6
<212> TYPE: PRT
<213> ORGANISM: Artificial Sequence
<220> FEATURE:
<223> OTHER INFORMATION: Synthesized

<400> SEQUENCE: 1

Gln Gly Ile Asn Asn Tyr
1               5

<210> SEQ ID NO 2
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: SITE
<222> LOCATION: (4)..(4)
<223> OTHER INFORMATION: X-any amino acid

<400> SEQUENCE: 2

Tyr Thr Ser Xaa
1

<210> SEQ ID NO 3
<211> LENGTH: 9
<212> TYPE: PRT
<213> ORGANISM: Artificial Sequence
<220> FEATURE:
<223> OTHER INFORMATION: Synthesized

<400> SEQUENCE: 3

Gln Gln Tyr Ser Lys Leu Pro Arg Thr
1               5
```

```
<210> SEQ ID NO 4
<211> LENGTH: 8
<212> TYPE: PRT
<213> ORGANISM: Artificial Sequence
<220> FEATURE:
<223> OTHER INFORMATION: Synthesized

<400> SEQUENCE: 4

Gly Tyr Thr Phe Ser Asn Tyr Trp
1               5

<210> SEQ ID NO 5
<211> LENGTH: 9
<212> TYPE: PRT
<213> ORGANISM: Artificial Sequence
<220> FEATURE:
<223> OTHER INFORMATION: Synthesized

<400> SEQUENCE: 5

Ile Leu Pro Gly Thr Gly Arg Thr Ile
1               5

<210> SEQ ID NO 6
<211> LENGTH: 15
<212> TYPE: PRT
<213> ORGANISM: Artificial Sequence
<220> FEATURE:
<223> OTHER INFORMATION: Synthesized

<400> SEQUENCE: 6

Ala Arg Arg Asp Tyr Tyr Gly Asn Phe Tyr Tyr Ala Met Asp Tyr
1               5                   10                  15

<210> SEQ ID NO 7
<211> LENGTH: 6
<212> TYPE: PRT
<213> ORGANISM: Artificial Sequence
<220> FEATURE:
<223> OTHER INFORMATION: Synthesized

<400> SEQUENCE: 7

Gln Ser Val Ser Ser Tyr
1               5

<210> SEQ ID NO 8
<211> LENGTH: 4
<212> TYPE: PRT
<213> ORGANISM: Artificial Sequence
<220> FEATURE:
<223> OTHER INFORMATION: Synthesized
<220> FEATURE:
<221> NAME/KEY: site
<222> LOCATION: (4)..(4)
<223> OTHER INFORMATION: X-any amino acid

<400> SEQUENCE: 8

Asp Ala Ser Xaa
1

<210> SEQ ID NO 9
<211> LENGTH: 9
<212> TYPE: PRT
<213> ORGANISM: Artificial Sequence
<220> FEATURE:
<223> OTHER INFORMATION: Synthesized
```

```
<400> SEQUENCE: 9

Gln Gln Arg Ser Asn Trp Pro Pro Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthesized

<400> SEQUENCE: 10

Gly Phe Thr Phe Asn Ser Phe Ala
1               5

<210> SEQ ID NO 11
<211> LENGTH: 9
<212> TYPE: PRT
<213> ORGANISM: Artificial Sequence
<220> FEATURE:
<223> OTHER INFORMATION: Synthesized

<400> SEQUENCE: 11

Ile Ser Gly Ser Gly Gly Gly Thr Tyr
1               5

<210> SEQ ID NO 12
<211> LENGTH: 15
<212> TYPE: PRT
<213> ORGANISM: Artificial Sequence
<220> FEATURE:
<223> OTHER INFORMATION: Synthesized

<400> SEQUENCE: 12

Ala Lys Asp Lys Ile Leu Trp Phe Gly Glu Pro Val Phe Asp Tyr
1               5                   10                  15

<210> SEQ ID NO 13
<211> LENGTH: 107
<212> TYPE: PRT
<213> ORGANISM: Artificial Sequence
<220> FEATURE:
<223> OTHER INFORMATION: Synthesized

<400> SEQUENCE: 13

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys
            100                 105
```

```
<210> SEQ ID NO 14
<211> LENGTH: 122
<212> TYPE: PRT
<213> ORGANISM: Artificial Sequence
<220> FEATURE:
<223> OTHER INFORMATION: Synthesized

<400> SEQUENCE: 14

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
    50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser
        115                 120

<210> SEQ ID NO 15
<211> LENGTH: 107
<212> TYPE: PRT
<213> ORGANISM: Artificial Sequence
<220> FEATURE:
<223> OTHER INFORMATION: Synthesized

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: Synthesized

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30
```

```
Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120

<210> SEQ ID NO 17
<211> LENGTH: 14
<212> TYPE: PRT
<213> ORGANISM: Artificial Sequence
<220> FEATURE:
<223> OTHER INFORMATION: Synthesized

<400> SEQUENCE: 17

Gly Ser Thr Ser Gly Ser Gly Lys Ser Ser Glu Gly Lys Gly
1               5                   10

<210> SEQ ID NO 18
<211> LENGTH: 243
<212> TYPE: PRT
<213> ORGANISM: Artificial Sequence
<220> FEATURE:
<223> OTHER INFORMATION: Synthesized

<400> SEQUENCE: 18

Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Gly Ser Thr Ser Gly
            100                 105                 110

Ser Gly Lys Ser Ser Glu Gly Lys Gly Gln Val Gln Leu Gln Gln Ser
        115                 120                 125

Gly Ser Glu Leu Met Met Pro Gly Ala Ser Val Lys Ile Ser Cys Lys
    130                 135                 140

Ala Thr Gly Tyr Thr Phe Ser Asn Tyr Trp Ile Glu Trp Val Lys Gln
145                 150                 155                 160

Arg Pro Gly His Gly Leu Glu Trp Ile Gly Glu Ile Leu Pro Gly Thr
                165                 170                 175

Gly Arg Thr Ile Tyr Asn Glu Lys Phe Lys Gly Lys Ala Thr Phe Thr
            180                 185                 190

Ala Asp Ile Ser Ser Asn Thr Val Gln Met Gln Leu Ser Ser Leu Thr
        195                 200                 205
```

```
Ser Glu Asp Ser Ala Val Tyr Tyr Cys Ala Arg Arg Asp Tyr Tyr Gly
        210                 215                 220

Asn Phe Tyr Tyr Ala Met Asp Tyr Trp Gly Gln Gly Thr Ser Val Thr
225                 230                 235                 240

Val Ser Ser

<210> SEQ ID NO 19
<211> LENGTH: 243
<212> TYPE: PRT
<213> ORGANISM: Artificial Sequence
<220> FEATURE:
<223> OTHER INFORMATION: Synthesized

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Gly Ser Thr Ser Gly
            100                 105                 110

Ser Gly Lys Ser Ser Glu Gly Lys Gly Glu Val Gln Leu Leu Glu Ser
        115                 120                 125

Gly Gly Gly Leu Val Gln Pro Gly Gly Ser Leu Arg Leu Ser Cys Ala
    130                 135                 140

Val Ser Gly Phe Thr Phe Asn Ser Phe Ala Met Ser Trp Val Arg Gln
145                 150                 155                 160

Ala Pro Gly Lys Gly Leu Glu Trp Val Ser Ala Ile Ser Gly Ser Gly
                165                 170                 175

Gly Gly Thr Tyr Tyr Ala Asp Ser Val Lys Gly Arg Phe Thr Ile Ser
            180                 185                 190

Arg Asp Asn Ser Lys Asn Thr Leu Tyr Leu Gln Met Asn Ser Leu Arg
        195                 200                 205

Ala Glu Asp Thr Ala Val Tyr Phe Cys Ala Lys Asp Lys Ile Leu Trp
    210                 215                 220

Phe Gly Glu Pro Val Phe Asp Tyr Trp Gly Gln Gly Thr Leu Val Thr
225                 230                 235                 240

Val Ser Ser

<210> SEQ ID NO 20
<211> LENGTH: 22
<212> TYPE: PRT
<213> ORGANISM: Artificial Sequence
<220> FEATURE:
<223> OTHER INFORMATION: Synthesized
```

```
<400> SEQUENCE: 20

Met Asp Phe Gln Val Gln Ile Phe Ser Phe Leu Leu Ile Ser Ala Ser
1               5                   10                  15

Val Ile Met Ser Arg Gly
            20

<210> SEQ ID NO 21
<211> LENGTH: 772
<212> TYPE: PRT
<213> ORGANISM: Artificial Sequence
<220> FEATURE:
<223> OTHER INFORMATION: Synthesized

<400> SEQUENCE: 21

Met Asp Phe Gln Val Gln Ile Phe Ser Phe Leu Leu Ile Ser Ala Ser
1               5                   10                  15

Val Ile Met Ser Arg Gly Asp Ile Gln Met Thr Gln Ser Thr Ser Ser
            20                  25                  30

Leu Ser Ala Ser Leu Gly Asp Arg Val Thr Ile Ser Cys Ser Ala Ser
        35                  40                  45

Gln Gly Ile Asn Asn Tyr Leu Asn Trp Tyr Gln Gln Lys Pro Asp Gly
    50                  55                  60

Thr Val Glu Leu Leu Ile Tyr Tyr Thr Ser Thr Leu Gln Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Pro Glu Asp Ile Gly Thr Tyr Tyr Cys Gln Gln
            100                 105                 110

Tyr Ser Lys Leu Pro Arg Thr Phe Gly Gly Gly Thr Lys Leu Glu Ile
        115                 120                 125

Lys Gly Ser Thr Ser Gly Ser Gly Lys Ser Ser Glu Gly Lys Gly Gln
    130                 135                 140

Val Gln Leu Gln Gln Ser Gly Ser Glu Leu Met Met Pro Gly Ala Ser
145                 150                 155                 160

Val Lys Ile Ser Cys Lys Ala Thr Gly Tyr Thr Phe Ser Asn Tyr Trp
                165                 170                 175

Ile Glu Trp Val Lys Gln Arg Pro Gly His Gly Leu Glu Trp Ile Gly
            180                 185                 190

Glu Ile Leu Pro Gly Thr Gly Arg Thr Ile Tyr Asn Glu Lys Phe Lys
        195                 200                 205

Gly Lys Ala Thr Phe Thr Ala Asp Ile Ser Ser Asn Thr Val Gln Met
    210                 215                 220

Gln Leu Ser Ser Leu Thr Ser Glu Asp Ser Ala Val Tyr Tyr Cys Ala
225                 230                 235                 240

Arg Arg Asp Tyr Tyr Gly Asn Phe Tyr Tyr Ala Met Asp Tyr Trp Gly
                245                 250                 255

Gln Gly Thr Ser Val Thr Val Ser Ser Ala Ala Lys Gly Lys His
            260                 265                 270

Leu Cys Pro Ser Pro Leu Phe Pro Gly Pro Ser Lys Pro Phe Trp Val
        275                 280                 285

Leu Val Val Val Gly Gly Val Leu Ala Cys Tyr Ser Leu Leu Val Thr
    290                 295                 300

Val Ala Phe Ile Ile Phe Trp Val Arg Ser Lys Arg Ser Arg Leu Leu
305                 310                 315                 320
```

-continued

```
His Ser Asp Tyr Met Asn Met Thr Pro Arg Pro Gly Thr Arg
                325                 330             335

Lys His Tyr Gln Pro Tyr Ala Pro Pro Arg Asp Phe Ala Ala Tyr Arg
            340             345                 350

Ser Gly Ser Gly Glu Gly Arg Gly Ser Leu Leu Thr Cys Gly Asp Val
        355                 360                 365

Glu Glu Asn Pro Gly Pro Tyr Val Met Asp Phe Gln Val Gln Ile Phe
370                 375                 380

Ser Phe Leu Leu Ile Ser Ala Ser Val Ile Met Ser Arg Gly Glu Ile
385                 390                 395                 400

Val Leu Thr Gln Ser Pro Ala Thr Leu Ser Leu Ser Pro Gly Glu Arg
                405                 410                 415

Ala Thr Leu Ser Cys Arg Ala Ser Gln Ser Val Ser Ser Tyr Leu Ala
            420                 425                 430

Trp Tyr Gln Gln Lys Pro Gly Gln Ala Pro Arg Leu Leu Ile Tyr Asp
        435                 440                 445

Ala Ser Asn Arg Ala Thr Gly Ile Pro Ala Arg Phe Ser Gly Ser Gly
    450                 455                 460

Ser Gly Thr Asp Phe Thr Leu Thr Ile Ser Ser Leu Glu Pro Glu Asp
465                 470                 475                 480

Phe Ala Val Tyr Tyr Cys Gln Gln Arg Ser Asn Trp Pro Pro Thr Phe
                485                 490                 495

Gly Gln Gly Thr Lys Val Glu Ile Lys Gly Ser Thr Ser Gly Ser Gly
            500                 505                 510

Lys Ser Ser Glu Gly Lys Gly Glu Val Gln Leu Leu Glu Ser Gly Gly
        515                 520                 525

Gly Leu Val Gln Pro Gly Gly Ser Leu Arg Leu Ser Cys Ala Val Ser
    530                 535                 540

Gly Phe Thr Phe Asn Ser Phe Ala Met Ser Trp Val Arg Gln Ala Pro
545                 550                 555                 560

Gly Lys Gly Leu Glu Trp Val Ser Ala Ile Ser Gly Ser Gly Gly Gly
                565                 570                 575

Thr Tyr Tyr Ala Asp Ser Val Lys Gly Arg Phe Thr Ile Ser Arg Asp
            580                 585                 590

Asn Ser Lys Asn Thr Leu Tyr Leu Gln Met Asn Ser Leu Arg Ala Glu
        595                 600                 605

Asp Thr Ala Val Tyr Phe Cys Ala Lys Asp Lys Ile Leu Trp Phe Gly
    610                 615                 620

Glu Pro Val Phe Asp Tyr Trp Gly Gln Gly Thr Leu Val Thr Val Ser
625                 630                 635                 640

Ser Leu Ser Asn Ser Ile Met Tyr Phe Ser His Phe Val Pro Val Phe
                645                 650                 655

Leu Pro Ala Lys Pro Thr Thr Thr Pro Ala Pro Arg Pro Pro Thr Pro
            660                 665                 670

Ala Pro Thr Ile Ala Ser Gln Pro Leu Ser Leu Arg Pro Glu Ala Cys
        675                 680                 685

Arg Pro Ala Ala Gly Gly Ala Val His Thr Arg Gly Leu Asp Phe Ala
    690                 695                 700

Cys Asp Ile Tyr Ile Trp Ala Pro Leu Ala Gly Thr Cys Gly Val Leu
705                 710                 715                 720

Leu Leu Ser Leu Val Ile Thr Leu Tyr Cys Asn His Arg Ser Gln Val
                725                 730                 735
```

```
Arg Lys Ala Ala Ile Thr Ser Tyr Glu Lys Ser Asp Gly Val Tyr Thr
                740                 745                 750

Gly Leu Ser Thr Arg Asn Gln Glu Thr Tyr Glu Thr Leu Lys His Glu
        755                 760                 765

Lys Pro Pro Gln
    770

<210> SEQ ID NO 22
<211> LENGTH: 40
<212> TYPE: PRT
<213> ORGANISM: Artificial Sequence
<220> FEATURE:
<223> OTHER INFORMATION: Synthesized

<400> SEQUENCE: 22

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 23
<211> LENGTH: 40
<212> TYPE: PRT
<213> ORGANISM: Artificial Sequence
<220> FEATURE:
<223> OTHER INFORMATION: Synthesized

<400> SEQUENCE: 23

Arg Ser Gln Val Arg Lys Ala Ala Ile Thr Ser Tyr Glu Lys Ser Asp
1               5                   10                  15

Gly Val Tyr Thr Gly Leu Ser Thr Arg Asn Gln Glu Thr Tyr Glu Thr
            20                  25                  30

Leu Lys His Glu Lys Pro Pro Gln
        35                  40

<210> SEQ ID NO 24
<211> LENGTH: 353
<212> TYPE: PRT
<213> ORGANISM: Artificial Sequence
<220> FEATURE:
<223> OTHER INFORMATION: Synthesized

<400> SEQUENCE: 24

Met Asp Phe Gln Val Gln Ile Phe Ser Phe Leu Leu Ile Ser Ala Ser
1               5                   10                  15

Val Ile Met Ser Arg Gly Asp Ile Gln Met Thr Gln Ser Thr Ser Ser
            20                  25                  30

Leu Ser Ala Ser Leu Gly Asp Arg Val Thr Ile Ser Cys Ser Ala Ser
        35                  40                  45

Gln Gly Ile Asn Asn Tyr Leu Asn Trp Tyr Gln Gln Lys Pro Asp Gly
    50                  55                  60

Thr Val Glu Leu Leu Ile Tyr Tyr Thr Ser Thr Leu Gln Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Pro Glu Asp Ile Gly Thr Tyr Tyr Cys Gln Gln
            100                 105                 110
```

Tyr Ser Lys Leu Pro Arg Thr Phe Gly Gly Thr Lys Leu Glu Ile
            115                 120                 125

Lys Gly Ser Thr Ser Gly Ser Gly Lys Ser Ser Glu Gly Lys Gly Gln
130                 135                 140

Val Gln Leu Gln Gln Ser Gly Ser Glu Leu Met Met Pro Gly Ala Ser
145                 150                 155                 160

Val Lys Ile Ser Cys Lys Ala Thr Gly Tyr Thr Phe Ser Asn Tyr Trp
                165                 170                 175

Ile Glu Trp Val Lys Gln Arg Pro Gly His Gly Leu Glu Trp Ile Gly
            180                 185                 190

Glu Ile Leu Pro Gly Thr Gly Arg Thr Ile Tyr Asn Glu Lys Phe Lys
        195                 200                 205

Gly Lys Ala Thr Phe Thr Ala Asp Ile Ser Ser Asn Thr Val Gln Met
    210                 215                 220

Gln Leu Ser Ser Leu Thr Ser Glu Asp Ser Ala Val Tyr Tyr Cys Ala
225                 230                 235                 240

Arg Arg Asp Tyr Tyr Gly Asn Phe Tyr Tyr Ala Met Asp Tyr Trp Gly
                245                 250                 255

Gln Gly Thr Ser Val Thr Val Ser Ser Ala Ala Ala Lys Gly Lys His
            260                 265                 270

Leu Cys Pro Ser Pro Leu Phe Pro Gly Pro Ser Lys Pro Phe Trp Val
        275                 280                 285

Leu Val Val Val Gly Gly Val Leu Ala Cys Tyr Ser Leu Leu Val Thr
    290                 295                 300

Val Ala Phe Ile Ile Phe Trp Val Arg Ser Lys Arg Ser Arg Leu Leu
305                 310                 315                 320

His Ser Asp Tyr Met Asn Met Thr Pro Arg Arg Pro Gly Pro Thr Arg
                325                 330                 335

Lys His Tyr Gln Pro Tyr Ala Pro Pro Arg Asp Phe Ala Ala Tyr Arg
            340                 345                 350

Ser

<210> SEQ ID NO 25
<211> LENGTH: 398
<212> TYPE: PRT
<213> ORGANISM: Artificial Sequence
<220> FEATURE:
<223> OTHER INFORMATION: Synthesized

<400> SEQUENCE: 25

Tyr Val Met Asp Phe Gln Val Gln Ile Phe Ser Phe Leu Leu Ile Ser
1               5                   10                  15

Ala Ser Val Ile Met Ser Arg Gly Glu Ile Val Leu Thr Gln Ser Pro
            20                  25                  30

Ala Thr Leu Ser Leu Ser Pro Gly Glu Arg Ala Thr Leu Ser Cys Arg
        35                  40                  45

Ala Ser Gln Ser Val Ser Ser Tyr Leu Ala Trp Tyr Gln Gln Lys Pro
    50                  55                  60

Gly Gln Ala Pro Arg Leu Leu Ile Tyr Asp Ala Ser Asn Arg Ala Thr
65                  70                  75                  80

Gly Ile Pro Ala Arg Phe Ser Gly Ser Gly Ser Gly Thr Asp Phe Thr
                85                  90                  95

Leu Thr Ile Ser Ser Leu Glu Pro Glu Asp Phe Ala Val Tyr Tyr Cys
            100                 105                 110

Gln Gln Arg Ser Asn Trp Pro Pro Thr Phe Gly Gln Gly Thr Lys Val
            115                 120                 125

Glu Ile Lys Gly Ser Thr Ser Gly Ser Gly Lys Ser Ser Glu Gly Lys
130                 135                 140

Gly Glu Val Gln Leu Leu Glu Ser Gly Gly Gly Leu Val Gln Pro Gly
145                 150                 155                 160

Gly Ser Leu Arg Leu Ser Cys Ala Val Ser Gly Phe Thr Phe Asn Ser
                165                 170                 175

Phe Ala Met Ser Trp Val Arg Gln Ala Pro Gly Lys Gly Leu Glu Trp
            180                 185                 190

Val Ser Ala Ile Ser Gly Ser Gly Gly Thr Tyr Tyr Ala Asp Ser
        195                 200                 205

Val Lys Gly Arg Phe Thr Ile Ser Arg Asp Asn Ser Lys Asn Thr Leu
    210                 215                 220

Tyr Leu Gln Met Asn Ser Leu Arg Ala Glu Asp Thr Ala Val Tyr Phe
225                 230                 235                 240

Cys Ala Lys Asp Lys Ile Leu Trp Phe Gly Glu Pro Val Phe Asp Tyr
                245                 250                 255

Trp Gly Gln Gly Thr Leu Val Thr Val Ser Ser Leu Ser Asn Ser Ile
            260                 265                 270

Met Tyr Phe Ser His Phe Val Pro Val Phe Leu Pro Ala Lys Pro Thr
        275                 280                 285

Thr Thr Pro Ala Pro Arg Pro Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Ser Leu Val Ile
            340                 345                 350

Thr Leu Tyr Cys Asn His Arg Ser Gln Val Arg Lys Ala Ala Ile Thr
        355                 360                 365

Ser Tyr Glu Lys Ser Asp Gly Val Tyr Thr Gly Leu Ser Thr Arg Asn
    370                 375                 380

Gln Glu Thr Tyr Glu Thr Leu Lys His Glu Lys Pro Pro Gln
385                 390                 395

<210> SEQ ID NO 26
<211> LENGTH: 20
<212> TYPE: PRT
<213> ORGANISM: Artificial Sequence
<220> FEATURE:
<223> OTHER INFORMATION: Synthesized

<400> SEQUENCE: 26

Gly Ser Gly Glu Gly Arg Gly Ser Leu Leu Thr Cys Gly Asp Val Glu
1               5                   10                  15

Glu Asn Pro Gly
            20

<210> SEQ ID NO 27
<211> LENGTH: 63
<212> TYPE: DNA
<213> ORGANISM: Artificial Sequence
<220> FEATURE:
<223> OTHER INFORMATION: Synthesized

<400> SEQUENCE: 27

```
ggctccggag agggcagagg aagtcttcta acatgcggtg acgtggagga gaatcccggc      60
cct                                                                   63
```

<210> SEQ ID NO 28
<211> LENGTH: 729
<212> TYPE: DNA
<213> ORGANISM: Artificial Sequence
<220> FEATURE:
<223> OTHER INFORMATION: Synthesized

<400> SEQUENCE: 28

```
gatatccaga tgacacagag tacatcctcc ctgtctgcct ctctgggaga cagagtcacc      60
atcagttgca gtgcaagtca gggcattaac aattatttaa actggtatca gcagaaacca     120
gatggaactg ttgaactcct gatctattac acatcaactt acagtcagg agtcccatca      180 aggttcagtg gcagtgggtc tgggacagat tattctctca ccatcagcaa cctggaacct     240
gaagatattg gcacttacta ttgtcagcag tatagtaagc ttcctcggac gttcggtgga     300
ggcaccaagc tggaaatcaa agggtcgact tccggtagcg gcaaatcctc tgaaggcaaa     360
ggtcaggttc agctgcagca gtctggatct gagctgatga tgcctggggc ctcagtgaag     420
atatcctgca aggctactgg ctacacattc agtaactact ggatagagtg gtaaagcag      480 aggcctggac atggccttga gtggattgga gagattttac ctggaactgg tagaactatc     540
tacaatgaga agttcaaggg caaggccaca ttcactgcag atatatcctc caacacagtc     600
caaatgcaac tcagcagcct gacatctgag gactctgccg tctattactg tgcaagaagg     660
gactattatg gtaacttta ctatgctatg gactactggg gtcaagggac ctcagtcacc      720
gtctcctca                                                             729
```

<210> SEQ ID NO 29
<211> LENGTH: 729
<212> TYPE: DNA
<213> ORGANISM: Artificial Sequence
<220> FEATURE:
<223> OTHER INFORMATION: Synthesized

<400> SEQUENCE: 29

```
gaaattgtgt tgacgcagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg cattccagcc     180
aggttcagtg gcagtgggtc tgggacagac ttcactctca ccatcagcag cctagagcct     240
gaagattttg cagtttatta ctgtcagcag cgtagcaact ggcctccgac gttcggccaa     300
gggaccaagg tggaaatcaa agggtcgact tccggtagcg gcaaatcctc tgaaggcaaa     360
ggtgaggtgc agctgttgga gtctggggga ggcttggtac agcctggggg gtccctgaga     420
ctctcctgtg cagtctctgg attcaccttt aacagctttg ccatgagctg ggtccgccag     480
gctccaggga aggggctgga gtgggtctca gctattagtg gtagtggtgg tggcacatac     540
tacgcagact ccgtgaaggg ccggttcacc atctccagag acaattccaa gaacacgctg     600
tatctgcaaa tgaacagcct gagagccgag gacacggccg tatatttctg tgcgaaagat     660 aagatttat ggtttgggga gccggtcttc gactactggg gccagggaac cctggtcacc      720
gtctcctca                                                             729
```

<210> SEQ ID NO 30
<211> LENGTH: 120
<212> TYPE: DNA
<213> ORGANISM: Artificial Sequence
<220> FEATURE:
<223> OTHER INFORMATION: Synthesized

<400> SEQUENCE: 30

```
agtaagagga gcaggctcct gcacagtgac tacatgaaca tgactccccg ccgccccggg    60
cccacccgca agcattacca gccctatgcc ccaccacgcg acttcgcagc ctatagatct   120
```

<210> SEQ ID NO 31
<211> LENGTH: 130
<212> TYPE: DNA
<213> ORGANISM: Artificial Sequence
<220> FEATURE:
<223> OTHER INFORMATION: Synthesized

<400> SEQUENCE: 31

```
agatctcaag tgcgaaaggc agctataacc agctatgaga aatcagatgg tgtttacacg    60
ggcctgagca ccaggaacca ggagacttac gagactctga agcatgagaa accaccacag   120
tagactcgag                                                          130
```

<210> SEQ ID NO 32
<211> LENGTH: 1059
<212> TYPE: DNA
<213> ORGANISM: Artificial Sequence
<220> FEATURE:
<223> OTHER INFORMATION: Synthesized

<400> SEQUENCE: 32

```
atggattttc aggtgcagat tttcagcttc ctgctaatca gtgcctcagt cataatgtcc    60
agaggagata tccagatgac acagagtaca tcctccctgt ctgcctctct gggagacaga   120
gtcaccatca gttgcagtgc aagtcagggc attaacaatt atttaaactg gtatcagcag   180
aaaccagatg gaactgttga actcctgatc tattacacat caactttaca gtcaggagtc   240
ccatcaaggt tcagtggcag tgggtctggg acagattatt ctctcaccat cagcaacctg   300
gaacctgaag atattggcac ttactattgt cagcagtata gtaagcttcc tcggacgttc   360
ggtggaggca ccaagctgga aatcaaaggg tcgacttccg gtagcggcaa atcctctgaa   420
ggcaaaggtc aggttcagct gcagcagtct ggatctgagc tgatgatgcc tggggcctca   480
gtgaagatat cctgcaaggc tactggctac acattcagta actactggat agagtgggta   540
aagcagaggc ctggacatgg ccttgagtgg attggagaga tttttacctgg aactggtaga   600
actatctaca tgagaagttt caagggcaag gccacattca ctgcagatat atcctccaac   660
acagtccaaa tgcaactcag cagcctgaca tctgaggact ctgccgtcta ttactgtgca   720
agaagggact attatggtaa ctttttactat gctatggact actggggtca agggacctca   780
gtcaccgtct cctcagcggc cgcaaaaggg aaacaccttt gtccaagtcc ctatttccc   840
ggaccttcta agccctttg ggtgctggtg gtggttggtg gagtcctggc ttgctatagc   900
ttgctagtaa cagtggcctt tattattttc tgggtgagga gtaagaggag caggctcctg   960
cacagtgact acatgaacat gactccccgc cgccccgggc ccacccgcaa gcattaccag  1020
ccctatgccc caccacgcga cttcgcagcc tatagatct                         1059
```

<210> SEQ ID NO 33
<211> LENGTH: 1198
<212> TYPE: DNA

<213> ORGANISM: Artificial Sequence
<220> FEATURE:
<223> OTHER INFORMATION: Synthesized

<400> SEQUENCE: 33

```
atggattttc aggtgcagat tttcagcttc ctgctaatca gtgcctcagt cataatgtcc      60
agaggagaaa ttgtgttgac gcagtctcca gccaccctgt ctttgtctcc aggggaaaga    120
gccaccctct cctgcagggc cagtcagagt gttagcagct acttagcctg gtaccaacag    180
aaacctggcc aggctcccag gctcctcatc tatgatgcat ccaacagggc cactggcatt    240
ccagccaggt tcagtggcag tgggtctggg acagacttca ctctcaccat cagcagccta    300
gagcctgaag attttgcagt ttattactgt cagcagcgta gcaactggcc tccgacgttc    360
ggccaaggga ccaaggtgga aatcaaaggg tcgacttccg gtagcggcaa atcctctgaa    420
ggcaaaggtg aggtgcagct gttggagtct gggggaggct tggtacagcc tggggggtcc    480
ctgagactct cctgtgcagt ctctggattc acctttaaca gctttgccat gagctgggtc    540
cgccaggctc agggaagggg ctggagtgg gtctcagcta ttagtggtag tggtggtggc    600
acatactacg cagactccgt gaagggccgg ttcaccatct ccagagacaa ttccaagaac    660
acgctgtatc tgcaaatgaa cagcctgaga gccgaggaca cggccgtata tttctgtgcg    720
aaagataaga ttttatggtt tggggagccg gtcttcgact actggggcca ggaaccctg    780
gtcaccgtct cctcactgag caactccatc atgtacttca gccacttcgt gccggtcttc    840
ctgccagcga agcccaccac gacgccagcg ccgcgaccac caacaccggc gcccaccatc    900
gcgtcgcagc ccctgtccct gcgcccagag gcgtgccggc cagcggcggg gggcgcagtg    960
cacacgaggg gctggactt cgcctgtgat atctacatct gggcgccctt ggccgggact   1020
tgtgggtcc ttctcctgtc actggttatc ccctttact gcaaccacag atctcaagtg   1080
cgaaaggcag ctataaccag ctatgagaaa tcagatggtg tttacacggg cctgagcacc   1140
aggaaccagg agacttacga gactctgaag catgagaaac caccacagta gactcgag    1198
```

<210> SEQ ID NO 34
<211> LENGTH: 2319
<212> TYPE: DNA
<213> ORGANISM: artificial sequenc
<220> FEATURE:
<223> OTHER INFORMATION: Synthesized

<400> SEQUENCE: 34

```
atggattttc aggtgcagat tttcagcttc ctgctaatca gtgcctcagt cataatgtcc      60
agaggagata tccagatgac acagagtaca tcctccctgt ctgcctctct gggagacaga    120
gtcaccatca gttgcagtgc aagtcagggc attaacaatt atttaaactg gtatcagcag    180
aaaccagatg gaactgttga actcctgatc tattacacat caactttaca gtcaggagtc    240
ccatcaaggt tcagtggcag tgggtctggg acagattatt ctctcaccat cagcaacctg    300
gaacctgaag atattggcac ttactattgt cagcagtata gtaagcttcc tcggacgttc    360
ggtggaggca ccaagctgga aatcaaaggg tcgacttccg gtagcggcaa atcctctgaa    420
ggcaaaggtc aggttcagct gcagcagtct ggatctgagc tgatgatgcc tggggcctca    480
gtgaagatat cctgcaaggc tactggctac acattcagta actactggat agagtgggta    540
aagcagaggc ctggacatgg ccttgagtgg attggagaga ttttacctgg aactggtaga    600
actatctaca tgagaagtt caagggcaag gccacattcc tgcagatat atcctccaac    660
acagtccaaa tgcaactcag cagcctgaca tctgaggact ctgccgtcta ttactgtgca    720
```

|  |  |
|---|---|
| agaagggact attatggtaa cttttactat gctatggact actggggtca agggacctca | 780 |
| gtcaccgtct cctcagcggc cgcaaaaggg aaacacctTt gtccaagtcc cctatttccc | 840 |
| ggaccttcta agccctTttg ggtgctggtg gtggttggtg gagtcctggc ttgctatagc | 900 |
| ttgctagtaa cagtggcctt tattattttc tgggtgagga gtaagaggag caggctcctg | 960 |
| cacagtgact acatgaacat gactccccgc cgccccgggc ccacccgcaa gcattaccag | 1020 |
| ccctatgccc caccacgcga cttcgcagcc tatagatctg gctccggaga gggcagagga | 1080 |
| agtcttctaa catgcggtga cgtggaggag aatcccggcc cttacgtaat ggattttcag | 1140 |
| gtgcagattt tcagcttcct gctaatcagt gcctcagtca taatgtccag aggagaaatt | 1200 |
| gtgttgacgc agtctccagc caccctgtct ttgtctccag gggaagagc caccctctcc | 1260 |
| tgcagggcca gtcagagtgt tagcagctac ttagcctggt accaacagaa acctggccag | 1320 |
| gctcccaggc tcctcatcta tgatgcatcc aacagggcca ctggcattcc agccaggttc | 1380 |
| agtggcagtg ggtctgggac agacttcact ctcaccatca gcagcctaga gcctgaagat | 1440 |
| tttgcagttt attactgtca gcagcgtagc aactggcctc cgacgttcgg ccaagggacc | 1500 |
| aaggtggaaa tcaaagggtc gacttccggt agcggcaaat cctctgaagg caaaggtgag | 1560 |
| gtgcagctgt tggagtctgg gggaggcttg gtacagcctg gggggtccct gagactctcc | 1620 |
| tgtgcagtct ctggattcac ctttaacagc tttgccatga gctgggtccg ccaggctcca | 1680 |
| gggaagggc tggagtgggt ctcagctatt agtggtagtg gtggtggcac atactacgca | 1740 |
| gactccgtga agggccggtt caccatctcc agagacaatt ccaagaacac gctgtatctg | 1800 |
| caaatgaaca gcctgagagc cgaggacacg gccgtatatt tctgtgcgaa agataagatt | 1860 |
| ttatggtttg gggagccggt cttcgactac tggggccagg gaaccctggt caccgtctcc | 1920 |
| tcactgagca actccatcat gtacttcagc cacttcgtgc cggtcttcct gccagcgaag | 1980 |
| cccaccacga cgccagcgcc gcgaccacca acaccggcgc ccaccatcgc gtcgcagccc | 2040 |
| ctgtccctgc gcccagaggc gtgccggcca cggcggggg gcgcagtgca cacgaggggg | 2100 |
| ctggacttcg cctgtgatat ctacatctgg gcgcccttgg ccgggacttg tggggtcctt | 2160 |
| ctcctgtcac tggttatcac cctttactgc aaccacagat ctcaagtgcg aaaggcagct | 2220 |
| ataaccagct atgagaaatc agatggtgtt tacacgggcc tgagcaccag gaaccaggag | 2280 |
| acttacgaga ctctgaagca tgagaaacca ccacagtag | 2319 |

<210> SEQ ID NO 35
<211> LENGTH: 45
<212> TYPE: PRT
<213> ORGANISM: Artificial Sequence
<220> FEATURE:
<223> OTHER INFORMATION: Synthesized

<400> SEQUENCE: 35

Lys Gly Lys His Leu Cys Pro Ser Pro Leu Phe Pro Gly Pro Ser Lys
1               5                   10                  15

Pro Phe Trp Val Leu Val Val Gly Gly Val Leu Ala Cys Tyr Ser
            20                  25                  30

Leu Leu Val Thr Val Ala Phe Ile Ile Phe Trp Val Arg
        35                  40                  45

<210> SEQ ID NO 36
<211> LENGTH: 91
<212> TYPE: PRT
<213> ORGANISM: Artificial Sequence

```
<220> FEATURE:
<223> OTHER INFORMATION: Synthesized

<400> SEQUENCE: 36

Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp Phe Ala Cys
    50                  55                  60

Asp Ile Tyr Ile Trp Ala Pro Leu Ala Gly Thr Cys Gly Val Leu Leu
65              70                  75                  80

Leu Ser Leu Val Ile Thr Leu Tyr Cys Asn His
                85                  90

<210> SEQ ID NO 37
<211> LENGTH: 134
<212> TYPE: DNA
<213> ORGANISM: artificial sequence
<220> FEATURE:
<223> OTHER INFORMATION: Synthesized

<400> SEQUENCE: 37
aaagggaaac acctttgtcc aagtcccta  tttcccggac cttctaagcc cttttgggtg    60
ctggtggtgg ttggtggagt cctggcttgc tatagcttgc tagtaacagt ggcctttatt   120
attttctggg tgag                                                     134

<210> SEQ ID NO 38
<211> LENGTH: 273
<212> TYPE: DNA
<213> ORGANISM: Artificial Sequence
<220> FEATURE:
<223> OTHER INFORMATION: Synthesized

<400> SEQUENCE: 38
ctgagcaact ccatcatgta cttcagccac ttcgtgccgg tcttcctgcc agcgaagccc    60
accacgacgc cagcgccgcg accaccaaca ccggcgccca ccatcgcgtc gcagcccctg   120
tccctgcgcc cagaggcgtg ccggccagcg gcggggggcg cagtgcacac gagggggctg   180
gacttcgcct gtgatatcta catctgggcg cccttggccg ggacttgtgg ggtccttctc   240
ctgtcactgg ttatcaccct ttactgcaac cac                                273

<210> SEQ ID NO 39
<211> LENGTH: 66
<212> TYPE: DNA
<213> ORGANISM: Artificial Sequence
<220> FEATURE:
<223> OTHER INFORMATION: Synthesized

<400> SEQUENCE: 39
atggattttc aggtgcagat tttcagcttc ctgctaatca gtgcctcagt cataatgtcc    60
agagga                                                              66
```

T-CELLS COMPRISING ANTI-CD38 AND ANTI-CD138 CHIMERIC ANTIGEN RECEPTORS AND USES THEREOF

CROSS-REFERENCE TO RELATED APPLICATION

This application is a National Phase of International Application No. PCT/IL2018/051325 filed Dec. 4, 2018, which claims priority to U.S. Provisional Patent Application No. 62/594,577 filed Dec. 5, 2017 and U.S. Provisional Patent Application No. 62/667,638 filed May 7, 2018, the disclosures of which are each incorporated herein, in their entirety, by this reference.

FIELD OF THE INVENTION

The present inventions relates to T-cells expressing at least two chimeric antigen receptors (CAR), wherein one of the CARs binds specifically to CD138 and another CAR binds specifically to CD38. The invention relates also to pharmaceutical compositions comprising said cells, their use in treating cancer, in particular the use treating multiple myeloma.

SEQUENCE LISTING

A sequence listing, titled 2020-08-14_Corrected_Sequence_Listing.txt, created 14 Aug. 2020, and comprising 38419 bytes, is submitted as a .txt file and hereby incorporated by reference.

BACKGROUND OF THE INVENTION

Chimeric antigen receptor T-cell (CAR-T) therapy is a newly developed adoptive antitumor treatment. Genetically modified T cells express chimeric antigen receptors, which generally consist of a signaling end domain (such as CD3-zeta or gamma chain from the FcR), transmembrane domain and an extracellular single-chain variable fragment (scFv) derived from a monoclonal antibody which gives the receptor specificity for a tumor-associated antigen on a target malignant cell. Upon binding the tumor-associated antigen via the chimeric antigen receptor, the chimeric antigen receptor expressed on T cell (CAR T-cell) mounts an immune response that is cytotoxic to the malignant cell. Theoretically, CAR-T cells can specifically localize and eliminate tumor cells by interacting with the tumor-associated antigens (TAAs) expressed on tumor cell surface.

Despite the fast growth in the field, the development of efficient and safe CAR-T treatment encounters in many challenges. Many known and numerous yet unidentified factors are likely to contribute to the variability observed in clinical responses across trials and also between individual patients. The factors that have to be considered are for example in vivo fate of the T-cells, properties of a tumor and safety. To improve the safety and efficacy it was suggested to generate T-cells transduced with a CAR that provides suboptimal activation upon binding to one antigen and a chimeric costimulatory receptor that recognizes a second antigen (Kloss et al., 2013, Nature Biotechnology, 13, 71-75, WO 2014/055668 and WO 2015/142314). Additional factor, which is always one of the major obstacles when cancer treatment is concerned, is the choice of the target(s). Truly tumor specific surface antigens are hardly identified, and the implementation of effective mechanisms to mitigate life threatening and unexpected off-target toxicities is crucial.

Multiple Myeloma (MM) is an incurable plasma cell (PC) malignancy, which develops in the bone marrow, and eventually causes renal failure, immunosuppression with repeated infections, anemia and bone lesions. Current therapies, including proteasome inhibitors and immunomodulatory agents, have improved outcomes substantially in patients with multiple myeloma. Unfortunately, the majority of these patients have a relapse and have limited treatment options after exposure to these classes of agents. Although CAR-T therapy could, in principle, overcome some of the problems of the "classic" treatment of MM, the major roadblock in development of CAR T-cells therapy is their substantial on-target off-tissue toxicity. Only a few proteins, and virtually no cell surface antigens, are exclusively expressed by malignant cells, resulting in the undesired targeting of healthy tissues. Therefore, the search for antigens specifically expressed on tumor cells only has become a central objective in identifying CAR targets in MM. Several myeloma-related surface molecules were determined as potential targets that may be aimed via CAR therapies. These targets include CD38, CD40, CD44, CD47, CD54, CD56 CD138, CD200 CD307 and so on (Atanackovic, et al., British Journal of Haematology, 2016, 172, 685-698). However, none of these targets is present exclusively on the cancer cells thus a substantial off-target effect may be expected when using these targets for CAR-T cells therapy.

Chen et al., (Leukemia 2017, doi:10.1038/leu.2017.302) indicated that targeting BCMA and CS1 on myeloma cells can potentially be an effective strategy for augmenting the response against myeloma bulk disease.

CD38 is a 45-kD, type II transmembrane glycoprotein that associates with cell-surface receptors in lipid rafts, regulates cytoplasmic $Ca^{2+}$ flux, and mediates signal transduction in lymphoid and myeloid cells. CD38 is highly and uniformly expressed on myeloma cells and is expressed at relatively low levels on normal lymphoid and myeloid cells and in some tissues of non-hematopoietic origin, which makes it a potential target in the treatment of myeloma. Daratumumab (HuMax-CD38, GenMab), a human IgG1κ monoclonal antibody, binds to a unique CD38 epitope. Preclinical studies showed that daratumumab induced target-cell killing of CD38-expressing tumor cells by means of multiple mechanisms, including complement-mediated and antibody-dependent cell-mediated cytotoxic effects, antibody-dependent cellular phagocytosis, apoptosis, and to a lesser extent, inhibition of the enzymatic activity of CD38. Anti-CD38 monoclonal antibodies are described for examples in U.S. Pat. No. 7,829,673.

CD138 is a surface protein, which functions as an adhesion molecule binding to the extracellular matrix molecules collagen and fibronectin. Anti-CD138 antibodies were previously described, for example in U.S. Pat. No. 9,221,914. Despite the fact that CD138 is considered as one of the most promising markers, in a phase I/II study with immunoconjugate BT062 used as a single agent, only 1 out of 23 patients showed an objective clinical response (Atanackovic et al.). Moreover, CD138 is expressed on many mature epithelial cells. Indeed liver and skin toxicity was observed in those clinical trials indicating that significant side effects of CAR-T treatment directing CD138 may be expected.

Other targets described above also have their merits as well as drawbacks, most of which are related to high level of side effects, that maintains the choice of the target as one of the major obstacles in developing safe and efficient CAR-T therapies. There is an unmet need in rational devel-

SUMMARY OF THE INVENTION opment of additional CAR T therapeutic systems allowing long lasting safe treatment of multiple myeloma with fewer off-target side effects.

It is now disclosed according to the present invention that T-cells genetically modified to express two separate distinct CARs capable of binding to two different carefully chosen targets on multiple myeloma cells, i.e. CD38 and CD138, effectively treated the cancer and extended survival. Moreover, the specific design of the CAR system, in which one CAR carried only an activation domain and the second CAR carried only a co-stimulating domain, allowed reducing the severity of side effect related to "on target off tumor" biding of the T-cells. Such a design allowed obtaining an efficient treatment having a reduced side effects. According to one aspect, the present invention provides a T-cell genetically modified to express at least two distinct and separate chimeric antigen receptors (CARs), wherein the first CAR comprises an antigen binding domain that binds specifically to CD138 and the second CAR comprises an antigen binding domain that binds specifically to CD38. According to some embodiments, the antigen binding domains binding specifically to CD38 or CD138 are single chain variable domains (scFv) of anti-CD38 and anti-CD138 antibodies, respectively. Thus according to one embodiment, the present invention provides a T-cell genetically modified to express two distinct and separate chimeric antigen receptors (CARs), wherein the first CAR comprises an anti-CD138 scFv and the second CAR anti-CD38 scFv.

According to some embodiments, the anti-CD138 scFv comprises a $V_L$ domain having the amino acid sequence SEQ ID NO: 13 or an analog thereof and a $V_H$ domain having the amino acid sequence SEQ ID NO: 14 or an analog thereof, wherein the $V_L$ and the $V_H$ domains of the anti-CD138 scFv are bound by a peptide linker and wherein the analog has at least 70% identity to the parent (original) sequence.

According to other embodiments, the anti-CD38 scFv domain comprises a $V_L$ domain having the amino acid sequence SEQ ID NO: 15 or an analog thereof and a $V_H$ domain having the amino acid sequence SEQ ID NO: 16 or an analog thereof, wherein the $V_L$ and the $V_H$ domains of the anti-CD38 scFv are bound by a peptide linker and wherein the analog has at least 70% identity to the original sequence.

According to some embodiments, at least one of the CARs comprises a costimulatory domain and the other one of the CARs comprises an activation domain. According to one embodiment, the costimulatory domain is a costimulatory domain of CD28, 4-1BB, OX40, iCOS, CD27, CD80, CD70. According to other embodiments, the activation domain is selected from FcRγ and CD3-ζ.

According to some embodiments, the first CAR comprises a costimulatory domain and devoid of an activation domain and the second CAR comprises an activation domain and devoid of a costimulatory domain. According to one embodiment, the activation domain has the amino acid sequence SEQ ID NO: 23 or an analog thereof and the costimulatory domain has the amino acid sequence SEQ ID NO: 22 or an analog thereof.

According to some embodiments, the transmembrane domain of the first CAR has a sequence SEQ ID NO: 35 or an analog thereof. According to other embodiments, the transmembrane domain of the second CAR has a sequence SEQ ID NO: 36 or an analog thereof.

According to some embodiments, the present invention provides CAR T-cell engeneered to express two separate chimeric antigen receptors (CARs), wherein the first CAR has amino acid sequence SEQ ID NO: 24 or being an analog thereof, and the second CAR has amino acid sequence in SEQ ID NO: 25 or being an analog thereof.

According to one embodiment, the T-cell is a CD4+ T-cell. According to another embodiment, the T-cell is a CD8+ T-cell. According to any one of the above embodiments, the T-cell expresses the CARs of the present invention.

According to another aspect, the present invention provides a T-cell, comprising at least one copy of one or more DNA constructs encoding the two or more CARs of the present invention. According to one embodiment, the T-cell comprises at least one copy of a DNA construct encoding for: (A) from 5' to 3': (i) a leader peptide, (ii) anti-CD138 scFv, (iii) a transmembrane domain I, (iv) a costimulatory domain, an activation domain or both; and (B) from 5' to 3' (v) a leader peptide, (vi) anti-CD38 scFv domain, (vii) a transmembrane domain II and (viii) a costimulatory domain, an activation domain or both; wherein (A) and (B) are separated by a self-cleaving peptide.

According to some embodiments, the DNA construct encodes, from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-CD38 scFv domain, (viii) a transmembrane domain II and (ix) an activation domain. According to other embodiments, the DNA construct encodes, from 5' to 3', (i) a leader peptide, (ii) anti-CD38 scFv, (iii) a transmembrane domain II (iv) an activation domain, (v) a self-cleaving peptide, (vi) a leader peptide, (vii) anti-CD138 scFv domain, (viii) a transmembrane domain I and (ix) a costimulatory domain. According to some embodiments, the self-cleaving peptide is encoded by a DNA sequence SEQ ID NO: 27 or a variant thereof.

Alternatively the T-cell comprises two different DNA constructs encoding the CARs of the present invention, wherein the first DNA construct comprises a sequence encoding, from 5' to 3', (i) a leader peptide, (ii) anti-CD138 scFv, (iii) a transmembrane domain I and (iv) a costimulatory domain, an activation domain or both, and the second DNA construct comprises a sequence encoding, from 5' to 3' (i) a leader peptide, (ii) anti-CD38 scFv domain, (iii) a transmembrane domain II and (iv) a costimulatory domain, an activation domain or both.

According to any one of the above embodiments, the anti-CD138 scFv is encoded by a DNA sequence set forth in SEQ ID NO: 28 or a variant thereof. According to other embodiments, the anti-CD38 scFv is encoded by a DNA sequence SEQ ID NO: 29 or a variant thereof. According to a further embodiment, the costimulatory domain is encoded by a DNA sequence SEQ ID NO: 30 or a variant thereof. According to yet another embodiment, the activation domain is encoded by a DNA sequence SEQ ID NO: 31 or a variant thereof. According to some embodiments, the leader peptide is encoded by the DNA sequence SEQ ID NO: 39 or a variant thereof. According to some embodiments, the a transmembrane domain I is encoded by the DNA sequence set in SEQ ID NO: 37 or a variant thereof. According to some embodiments, the a transmembrane domain II is encoded by the DNA sequence set in SEQ ID NO: 38 or a variant thereof.

According to one embodiment, the present invention provides a T-cell comprising at least one copy of a DNA construct having the DNA sequence SEQ ID NO: 34 or a variant thereof.

According to other embodiments, the present invention provides a CAR T-cell comprising at least one copy of each one of two DNA constructs, wherein the first DNA construct comprises the DNA sequence SEQ ID NO: 32 or a variant thereof and the second DNA construct comprises the DNA sequence SEQ ID NO: 33 or a variant thereof.

According to another aspect, the present invention provides a DNA construct at least two distinct separate chimeric antigen receptors (CARs), wherein the first CAR comprises an antigen binding domain that binds specifically to CD138 and the second CAR comprises an antigen binding domain that binds specifically to CD38. According to one embodiment, the DNA construct encodes, from 5' to 3': (i) a leader peptide, (ii) anti-CD138 scFv, (iii) a transmembrane domain I, (iv) a costimulatory domain, an activation domain or both, (iv) a self-cleaving peptide, (vi) a leader peptide, (vii) anti-CD38 scFv domain, (viii) a transmembrane domain II and (ix) a costimulatory domain, an activation domain or both. According to one embodiment, the present invention provides a DNA construct comprising DNA sequence SEQ ID NO: 32 and DNA sequence SEQ ID NO: 33, or a variant thereof. According to another embodiment, the present invention provides a DNA construct comprising DNA sequence SEQ ID NO: 34 or a variant thereof.

According to another aspect, the present invention provides a vector comprising the DNA construct of the present invention. According to one embodiment, the vector comprises a DNA construct comprising DNA sequence SEQ ID NO: 32 and DNA sequence SEQ ID NO: 33, or a variant thereof. According to another embodiment, the vector comprises a DNA construct comprising DNA sequence SEQ ID NO: 34 or a variant thereof. According to some embodiments, the vector is a viral vector.

According to yet another aspect, the present invention provides a cell comprising the DNA construct of the vector of the present invention. According to one embodiment, the cell is prokaryotic cell. According to another embodiment, the cell is an eukaryotic cell. According to some embodiments, the cell is a human cell. According to another embodiment, the cell is T-cell, such as CD4+ or CD8+ T-cell.

According to another aspect, the present invention provides a pharmaceutical composition comprising a plurality of CAR T-cells of the present invention. According to one embodiment, the T-cells are genetically modified to express two CARs of the present invention. According to one embodiment, the T-cells express the CARs of the present invention. According to further embodiment, the T-cell comprises a DNA construct encoding the two CARs of the present invention or two or more different constructs encoding the two different CARs of the present invention. According to some embodiments, the pharmaceutical composition of the present invention is for use in treating cancer. According to one embodiment, the cancer is multiple myeloma. According to some embodiments, the T-cells are genetically modified to express two CARs having amino acid sequence SEQ ID NO: 24 and SEQ ID NO: 25.

According to another aspect, the present invention provides a method of treating cancer such as multiple myeloma in a subject in need thereof, comprising administering an effective amount of T-cells of the present invention. According to another aspect, the present invention provides a method for preparation of T-cells genetically modified to express at least two distinct separate chimeric antigen receptors (CARs), wherein the first CAR comprises an anti-CD38 scFv and the second CAR comprises an antigen anti-CD138 scFv, said method comprises transfecting T-cells with the DNA construct of the present invention.

BRIEF DESCRIPTION OF THE FIGURES

FIG. 3 shows stimulation of CAR T-cells by target cells expressing different levels of CD38 and CD138.

DETAILED DESCRIPTION OF THE INVENTION

Figure 1:
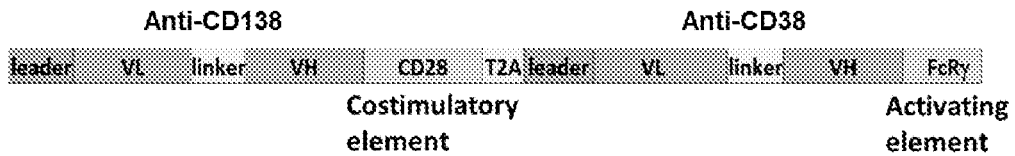
FIG. 1 shows a scheme of a dual-CAR DNA construct: $V_L$ and $V_H$ are parts of scFv separated by a linker, T2A is a self-cleaving peptide, CD28 refers to a costimulatory element of CD28, and FcRγ is an activation domain.

According to one aspect, the present invention provides a T-cell genetically modified to express at least two distinct separate chimeric antigen receptors (CARs), wherein the first CAR comprises an antigen-binding domain that binds specifically to human CD138 and the second CAR comprises an antigen binding domain that binds specifically to human CD38.

The term "T cell" as used herein refers a lymphocyte of a type produced or processed by the thymus gland that participates in a variety of cell-mediated immune reactions, as well known in art. The term encompasses T-cells transduces with a nucleic acid such as DNA or RNA polypeptide, optionally using a vector. The T-cells of the present invention are capable of expressing the CAR molecules encoded by the DNA or RNA by which the T-cells are transduced infected or electroporated.

The terms "chimeric antigen receptor" or "CAR" are used herein interchangeably and refer to engineered receptors, i.e. proteins, which are expressed onto cells. In general, a CAR comprises an extracellular domain (extracellular part) comprising the antigen binding domain, a transmembrane domain and an intracellular domain.

The extracellular domain comprises an antigen binding domain and optionally a spacer or hinge region.

The antigen binding domain of the CAR targets a specific antigen. The targeting regions may comprise full length heavy chain of an antibody, Fab fragments, or single chain variable fragment (scFv) of an antibody. The antigen binding domain can be derived from the same species or a different species for or in which the CAR will be used in. In one embodiment, the antigen binding domain is a scFv.

The extracellular spacer or hinge region of a CAR is located between the antigen binding domain and a transmembrane domain. Extracellular spacer domains may include, but are not limited to, Fc fragments of antibodies or fragments or derivatives thereof, hinge regions of antibodies or fragments or derivatives thereof, CH2 regions of antibodies, CH3 regions of antibodies, accessory proteins, artificial spacer sequences or combinations thereof.

The term "transmembrane domain" refers to the region of the CAR, which crosses or bridges the plasma membrane. The transmembrane domain of the CAR of the invention is the transmembrane region of a transmembrane protein, an artificial hydrophobic sequence or a combination thereof. According to some embodiments, the term comprises also transmembrane domain together with extracellular spacer or hinge region.

The terms "specifically binds" or "specific for" with respect to an antigen-binding domain of an antibody, of a fragment thereof or of a CAR refers to an antigen-binding domain which recognizes and binds to a specific antigen, but does not substantially recognize or bind other molecules in a sample. The term imply that the antigen-binding domain binds to its antigen with high affinity and binds other antigens with low affinity. An antigen-binding domain that binds specifically to an antigen from one species may bind also to that antigen from another species. This cross-species reactivity is not contrary to the definition of that antigen-binding domain as specific.

An intracellular domain may be an intracellular domain of T cell receptor or of any other receptor (e.g., TNFR superfamily member) or portion thereof, such as an intracellular activation domain (e.g., an immunoreceptor tyrosine-based activation motif (ITAM)-containing T cell activating motif), an intracellular costimulatory domain, or both.

The terms "genetically modified T cells" of the present invention and "CAR-T cells" are used herein interchangeably.

The terms "CD38" and "human CD38" are used herein interchangeably and refer to the protein known as human cluster of differentiation 38 (CD38), ADP-ribosyl cyclase 1, cADPr hydrolase 1, Cyclic ADP-ribose hydrolase 1, T10 and has an extension number EC 3.2.2.5. The terms "anti CD38" or "αCD38" refers to an antigen binding domain of an antibody that binds specifically to human CD38. According to one embodiment, antigen binding domain is an antigen binding domain of a CAR. According to another embodiments, the antigen binding domain is a scFv. According to a further embodiment, the antigen binding domain binds to an epitope of the human CD38, and in particular to an epitope of the extracellular domain of the human CD38.

The term "CD138" and "human CD138" are used herein interchangeably and refer to the protein known as Syndecan 1, SDC1, CD138, SDC, or SYND1, and having an accession number P18827. The terms "anti CD138" or "αCD138" refers to an antigen binding domain of an antibody that binds specifically to human CD138. According to one embodiment, antigen binding domain is an antigen binding domain of a CAR. According to another embodiments, the antigen binding domain is a scFv. According to a further embodiment, the antigen binding domain binds to an epitope of the human CD138, and in particular to an epitope of the extracellular domain of the human CD138.

According to some embodiments, the antigen binding domains of the CARs of the present invention are scFv. According to one embodiment, the present invention provides a T-cell genetically modified to express at least two distinct separate chimeric antigen receptors (CARs), wherein the first CAR comprises an scFv antigen binding domain that binds specifically to human CD138 (anti-CD138 scFv) and the second CAR comprises an scFv antigen binding domain that binds specifically to human CD38 (anti-CD38 scFv).

According to one embodiment, the present invention provides a T-cell genetically modified to express two distinct separate chimeric antigen receptors (CARs), wherein the first CAR comprises anti-CD138 scFv and the second CAR comprises anti-CD38 scFv. The term "first CAR" as used herein refers to a CAR comprising anti-CD138 scFv. The term "second CAR" as used herein refers to a CAR comprising anti-CD38 scFv.

According to any one of the above embodiments, anti-CD138 and anti-CD38 scFv binding domains comprise $V_L$ and $V_H$ domains.

According to one embodiment, the anti-CD138 scFv comprises $V_L$ and $V_H$ domains, wherein the $V_L$ domain comprises three complementarity determining regions (CDRs) having or consisting of the sequences SEQ ID NO: 1, 2 and 3 and the $V_H$ domain comprises three CDRs having or consisting of the sequences SEQ ID NO: 4, 5 and 6.

According to one embodiment, the anti-CD38 scFv comprises $V_L$ and $V_H$ domains, wherein the $V_L$ domain comprises three complementarity determining regions (CDRs) having or consisting of the sequences SEQ ID NO: 7, 8 and 9 and the $V_H$ domain comprises three CDRs having or consisting of the sequences SEQ ID NO: 10, 11 and 12.

According to some embodiments, the anti-CD138 scFv comprises 6 CDRs having or consisting of the sequences SEQ ID NO: 1, 2, 3, 4, 5 and 6, and the anti-CD138 scFv comprises 6 CDRs having or consisting of the sequences set forth in SEQ ID NO: 7, 8, 9, 10, 11 and 12.

According to any one of the aspects and embodiments of the invention, the terms "peptide comprising the amino acid sequence set forth in SEQ ID NO: X", "peptide comprising SEQ ID NO: X" and "peptide having SEQ ID NO: X" are used herein interchangeably. The terms "peptide consisting of the amino acid sequence set forth in SEQ ID NO: X", "peptide consisting of SEQ ID NO: X" and "peptide of SEQ ID NO: X" are used herein interchangeably.

According to any one of the above embodiments, the anti-CD138 scFv comprises a $V_L$ domain having the amino acid sequence SEQ ID NO: 13 or an analog thereof and a $V_H$ domain having the amino acid sequence SEQ ID NO: 14 or an analog thereof, wherein the $V_L$ and the $V_H$ domains of the anti-CD138 scFv are bound by a peptide linker and wherein the analog has at least 70% identity to the original sequence. According to one embodiment, the anti-CD138 scFv comprises a $V_L$ domain having the amino acid sequence SEQ ID NO: 13 and a $V_H$ domain having the amino acid sequence SEQ ID NO: 14. According to another embodiment, the $V_L$ domain is an analog of SEQ ID NO: 13. According to a further embodiment, the $V_H$ domain is an analog of SEQ ID NO: 14. According to some embodiments, the anti-CD138 scFv comprises a $V_L$ domain being an analog of SEQ ID NO: 13 and a $V_H$ domain being an analog of SEQ ID NO: 14.

According to any one of the above embodiments, the anti-CD38 scFv domain comprises a $V_L$ domain having the amino acid sequence SEQ ID NO: 15 or an analog thereof and a $V_H$ domain having the amino acid sequence SEQ ID NO: 16 or an analog thereof, wherein the $V_L$ and the $V_H$ domains of the anti-CD38 scFv are bound by a peptide linker and wherein the analog has at least 70% identity to the original sequence. According to one embodiment, the anti-CD38 scFv comprises a $V_L$ domain having the amino acid sequence SEQ ID NO: 15 and a $V_H$ domain having the amino acid sequence SEQ ID NO: 16. According to another embodiment, the $V_L$ domain is an analog of SEQ ID NO: 15. According to another embodiment, the $V_H$ domain is an analog of SEQ ID NO: 16. According to some embodiments, the anti-CD138 scFv comprises a $V_L$ domain being an analog of SEQ ID NO: 15 and a $V_H$ domain being an analog of SEQ ID NO: 16.

The term "peptide linker" refers to any peptide capable of connecting two variable domains with its length depending on the kinds of variable domains to be connected. According to some embodiments, the peptide linker is a peptide having the amino acid sequence SEQ ID NO: 17. According to another embodiment, the peptide linker is an analog of a peptide having SEQ ID NO: 17.

As described above, the scFv comprises a $V_H$ domain linked by a peptide linker to a $V_L$ domain. According to some embodiments, the $V_H$ is located N-terminally to $V_L$. According to another embodiment, the $V_L$ is located N-terminally to $V_H$.

According to some embodiments, the present invention provides T-cell genetically modified to express two CARs, wherein one CAR comprises an anti-CD138 scFv comprising a $V_L$ domain having SEQ ID NO: 13 and a $V_H$ domain having the amino acid sequence SEQ ID NO: 14, and the second CAR comprises an anti-CD38 scFv comprising a $V_L$ domain having SEQ ID NO: 15 and a $V_H$ domain having the amino acid sequence SEQ ID NO: 16. According to some embodiments, the $V_L$ and $V_H$ domains of anti-CD138 scFv and/or of anti-CD38 scFv are bound by a peptide linker having amino acid sequence SEQ ID NO: 17.

The term "peptide" refers to a short chain of amino acid residues linked by peptide bonds, i.e., a covalent bond formed between the carboxyl group of one amino acid and an amino group of an adjacent amino acid. The term "peptide" refers to short sequences having up to 50 amino acids. A chain of amino acids monomers longer than 50 amino acid is referred as a "polypeptide". Such polypeptides, when having more than 50 amino acid residues, can also be classified as proteins, more particularly, proteins of low or medium molecular weight.

The terms "peptide analog", "analog", "sequence analog", "analogous sequence" and "analog of SEQ ID NO: X" are used herein interchangeably and refer to an analog of a peptide having at least 70% sequence identity to the original peptide, wherein the analog retains the activity of the original peptide; X represents a number of the sequence. Thus, the terms "analog" and "active analog" may be used interchangeably. The term "analog" refer to a peptide or a protein that contains substitutions, rearrangements, deletions, additions and/or chemical modifications in the amino acid sequence of the parent (original) peptide or a protein, respectively. According to some embodiments, the peptide analog has at least 80%, at least 90% at least 95%, at least 98% or at least 99% sequence identity to the original peptide. According to some embodiments, the analog has about 80% to about 99%, about 85% to about 98% or about 90% to about 95% sequence identity to the original peptide. According to some embodiments, the analog of the present invention comprises the sequence of the original peptide in which 1, 2, 3, 4, or 5 substitutions were made.

The substitutions of the amino acids may be conservative or non-conservative substitution. The non-conservative substitution encompasses substitution of one amino acid by any other amino acid.

According to some embodiments, the term "analog" encompasses also the term "conservative analog".

Conservative substitutions of amino acids as known to those skilled in the art are within the scope of the present invention. Conservative amino acid substitutions include replacement of one amino acid with another having the same type of functional group or side chain, e.g., aliphatic, aromatic, positively charged, negatively charged. One of skill will recognize that individual substitutions, is a "conservatively modified analog" where the alteration results in the substitution of an amino acid with a chemically similar amino acid. Conservative substitution tables providing functionally similar amino acids are well known in the art. One typical example of conservative substitution is provided below.

The following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). In other embodiments, the conservative substitution encompass substitution with a chemically similar non-natural amino acid.

Thus, in some embodiments, the analog is a conservative analog of the scFv, either anti-CD38 or anti-CD138. According to some embodiments, the conservative analog of the present invention comprises the sequence of the original scFv in which 1, 2, 3, 4, or 5 conservative substitutions were made. According to another embodiment, the analog consists of the amino acid sequence of the original peptide in which 1, 2 or 3 conservative substitution were made. Thus, the analog consists of the amino acid sequence of the original peptide with 1, 2 or 3 conservative substitutions.

According to some embodiments, the anti-CD138 scFv has an amino acid sequence SEQ ID NO: 18. According to other embodiments, the anti CD138 scFv consists of amino acid sequence SEQ ID NO: 18.

According to other embodiments, the anti-CD38 scFv has amino acid sequence SEQ ID NO: 19. According to other embodiments, the anti-CD38 scFv consists of amino acid sequence SEQ ID NO: 19.

According to further embodiments, the anti-CD138 scFv has amino acid sequence SEQ ID NO: 18 and the anti-CD38 scFv has amino acid sequence SEQ ID NO: 19. According to another embodiment, the anti-CD138 scFv consists of the amino acid sequence SEQ ID NO: 18 and the anti-CD38 scFv consists of the amino acid sequence SEQ ID NO: 19.

According to any one of the above embodiments, the extracellular domain of the CARs comprises a leader peptide. According to one embodiment, the leader peptide is located N-terminally to scFv. The term "leader peptide", "lead peptide" and "signal peptide" are used herein interchangeable and refer to a peptide that translocates or prompts translocation of the target protein to cellular membrane.

According to one embodiment, the first CAR comprises a leader peptide comprising SEQ ID NO: 20 located N-terminally to anti-CD138 scFv. According to another embodiment, the leader peptide comprising SEQ ID NO: 20 is located N-terminally to anti-CD138 scFv comprising or consisting of SEQ ID NO: 18.

According to one embodiment, the second CAR comprises a leader peptide comprising SEQ ID NO: 20 located N-terminally to anti-CD38 scFv. According to another embodiment, the leader peptide comprising SEQ ID NO: 20 is located N-terminally to anti-CD38 scFv comprising or consisting of SEQ ID NO: 19.

According to any one of the above embodiments, at least one of the CARs comprises a costimulatory domain and at least one another CAR comprises an activation domain.

According to some embodiments, the first CAR comprises a costimulatory domain and the second CAR comprises an activation domain. According to some embodiments, the first CAR comprises an activation domain and the second CAR comprises a costimulatory domain.

According to some embodiments, the costimulatory domain is selected from a costimulatory domain of CD28, 4-1BB, OX40, iCOS, CD27, CD80 and CD70. According to one embodiment, the costimulatory domain is a costimulatory domain of CD28. According to another embodiment, the costimulatory domain has an amino acid sequence SEQ ID NO: 22. According to a further embodiment, the costimulatory domain is an analog of SEQ ID NO: 22.

The terms "activation domain" and "activating element" are used herein interchangeably and refer to an intracellular signaling domain. According to some embodiments, the activation domain is selected from FcRγ and CD3-ζ. According to one embodiment, the activation domain has the amino acid sequence SEQ ID NO: 23. According to a further embodiment, the activation domain is an analog of SEQ ID NO: 23.

According to the teaching of the present invention, it is beneficial to separate between a costimulatory domain and an activation domain in order to achieve lower "on target off tumor" effect. Thus, according to one embodiment, one CAR comprises only a costimulatory domain and the another CAR comprises only an activation domain. Thus, in one embodiment, the first CAR, comprising anti-CD138 scFv, comprises a costimulatory domain and devoid of an activation domain, and the second CAR comprising anti-CD38 scFv comprises an activation domain and devoid of a costimulatory domain. According to another embodiment, the first CAR comprises an activation domain and devoid of a costimulatory domain and the second CAR comprises a costimulatory domain and devoid of an activation domain.

According to a further embodiment, at least one of the CARs comprises both an activation domain and a costimulatory domain.

According to another embodiment, the second CAR comprises both an activation domain and a costimulatory domain. According to such embodiments, the first CAR comprises a costimulatory domain and devoid of an activation domain.

According to some embodiments, the activation domain has amino acid sequence SEQ ID NO: 23 and costimulatory domain has amino acid sequence SEQ ID NO: 22. According to one embodiment, the activation domain is an analog of SEQ ID NO: 23. According to a further embodiment, the costimulatory domain in an analog of SEQ ID NO: 22.

According to one embodiment, the first CAR comprises amino acid sequences SEQ ID NO: 18 and SEQ ID NO: 22. According to another embodiment, the second CAR comprises amino acid sequences SEQ ID NO: 19 and SEQ ID NO: 23. According to one embodiment, the present invention provides an engineered T-cell comprising two CARs, wherein the first CAR comprises amino acid sequences SEQ ID NO: 18 and SEQ ID NO: 22 and the second CAR comprises amino acid sequences SEQ ID NO: 19 and SEQ ID NO: 23.

According to any one of the above embodiments, the CARs comprises a transmembrane domain (TM) and a hinge domain. According to the teaching of the present invention when the reference made to a TM domain it includes also a hinge domain and sequences of the transmembrane domain include also the sequences of the hinge domains. According to one embodiment, the first CAR comprises a TM domain I (TM-I) having the amino acid sequence SEQ ID NO: 35. According to another embodiment, the second CAR comprises a TM domain II (TM-II) having the amino acid sequence SEQ ID NO: 36.

According to some embodiments, the present invention provides a T-cell engineered to express two chimeric antigen receptors (CARs), wherein the first CAR has the amino acid sequence set forth in SEQ ID NO: 24 and the second CAR has the amino acid sequence SEQ ID NO: 25. According to one embodiment, the first CAR has an amino acid sequence being an analog of SEQ ID NO: 24. According to another embodiment, the second CAR has an amino acid sequence being an analog of SEQ ID NO: 25. According to a further embodiment, the first CAR has the amino acid sequence analogous to SEQ ID NO: 24 and the second CAR has the amino acid sequence analogous to SEQ ID NO: 25. According to one embodiment, the present invention provides a T-cell engineered to express two chimeric antigen receptors (CARs), wherein the first CAR consists of amino acid sequence SEQ ID NO: 24 and the second CAR consists of amino acid sequence SEQ ID NO: 25. According to some embodiments, the variant has at least 85% sequence identity to original sequence. According to other embodiments, the variant has at least 90%, at least 95% or at least 98% sequence identity to original sequence.

According to any one of the above embodiments, the T cell is selected are from CD4+ T-cell and a CD8+ T-cell. Thus, in one embodiment, the present invention provides CD4+ T-cells genetically modified to express two distinct separate CARs, wherein the first CAR comprises anti-CD138 scFv and the second CAR comprises anti-CD38 scFv. According to another embodiment, the present invention provides CD8+ T-cells genetically modified to express two distinct separate CARs, wherein the first CAR comprises anti-CD138 scFv and the second CAR comprises anti-CD38 scFv. According to some such embodiments, the first CAR comprises amino acid sequences SEQ ID NO: 18 and SEQ ID NO: 22. According to another embodiment, the second CAR comprises amino acid sequences SEQ ID NO: 19 and SEQ ID NO: 23. According to one embodiment, the first CAR comprises amino acid sequences SEQ ID NO: 18 and SEQ ID NO: 22 and the second CAR comprises amino acid sequences SEQ ID NO: 19 and SEQ ID NO: 23. According to one such embodiments, the first CAR has the amino acid sequence SEQ ID NO: 24 or being an analog thereof and the second CAR has the amino acid sequence SEQ ID NO: 25 or being an analog thereof. According to a further embodiment, the present invention provides CD4+ and/or CD8+ T-cells genetically modified to express two distinct separate CARs, wherein the first CAR consists of amino acid sequence SEQ ID NO: 24 and the second CAR consists of amino acid sequence SEQ ID NO: 25.

According to any one of the above embodiments, the T-cells of the present invention are capable of expressing two distinct separate CARs, wherein the first CAR comprises anti-CD138 scFv and the second CAR comprises anti-CD38 scFv. According to some embodiments, the present intention provides the T-cells expressing two distinct separate CARs, wherein the first CAR comprises anti-CD138 scFv and the second CAR comprises anti-CD38 scFv. According to some embodiments, the T cell is selected from CD4+ T-cell and a CD8+ T-cell. Thus, in one embodiment, the present invention provides CD4+ T-cells expressing two distinct separate CARs, wherein the first CAR comprises anti-CD138 scFv and the second CAR comprises anti-CD38 scFv. According to another embodiment, the present invention provides CD8+ T-cells expressing two distinct separate CARs, wherein the first CAR comprises anti-CD138 scFv and the second CAR comprises anti-CD38 scFv. According to some such embodiments, the first CAR comprises amino acid sequences SEQ ID NO: 18 and SEQ ID NO: 22. According to another embodiment, the second CAR comprises amino acid sequences SEQ ID NO: 19 and SEQ ID NO: 23. According to one embodiment, the first CAR comprises amino acid sequences SEQ ID NO: 18 and SEQ ID NO: 22 and the second CAR comprises amino acid sequences SEQ ID NO: 19 and SEQ ID NO: 23. According to one such embodiments, the first CAR has the amino acid sequence SEQ ID NO: 24 or being an analog thereof and the second CAR has the amino acid sequence SEQ ID NO: 25 or being an analog thereof. According to a further embodiment, the present invention provides CD4+ and/or CD8+ T-cells expressing two distinct separate CARs, wherein the first CAR consists of amino acid sequence SEQ ID NO: 24 and the second CAR consists of amino acid sequence SEQ ID NO: 25.

According to another aspect, the present invention provides a T-cell comprising at least one copy of one or more DNA constructs encoding at least two distinct separate chimeric antigen receptors (CARs), wherein the first CAR comprises an antigen binding domain that binds specifically to CD138 and the second CAR comprises an antigen binding domain that binds specifically to CD38. According to one embodiment, the antigen binding domains of the CARs of the present invention are scFv. Thus, the T-cell comprises at least one copy of one or more DNA constructs encoding the at least two distinct separate chimeric antigen receptors (CARs), wherein the first CAR comprises an anti-CD138 scFv and the second CAR comprises anti-CD38 scFv. According to one embodiment, the two CARs are encoded by one DNA construct. According to another embodiment, the two CARs are encoded by two different DNA constructs. According to one embodiment, the T-cell expresses or capable of expressing the CARs of the present invention.

The term "DNA construct" as used herein refers to an artificially constructed segment of a nucleic acid. It can be an isolate or integrated in to another DNA molecule. Accordingly, a "recombinant DNA construct" is produced by laboratory methods. The term "nucleic acid" encompasses DNA, RNA, single stranded or double stranded and chemical modifications thereof. The terms "nucleic acid" and "polynucleotide" are used interchangeably herein.

The CARs of the present invention may be encoded by one DNA construct or by 2 or more DNA constructs.

According to some embodiments, the two CAR of the present invention are encoded by one DNA construct. Thus, in one embodiment, the present invention provides a T-cell comprising at least one copy of a DNA construct encoding for: (A) from 5' to 3', (i) a leader peptide, (ii) anti-CD138 scFv, (iii) a transmembrane domain I, (iv) a costimulatory domain, an activation domain or both, and (B) form 5' to 3' (v) a leader peptide, (vi) anti-CD38 scFv domain, (vii) a transmembrane domain II and (viii) a costimulatory domain, an activation domain or both; wherein (A) and (B) are separated by a self-cleaving peptide. According to one embodiment, the present invention provides a T-cell comprising at least one copy of a DNA construct encoding, from 5' to 3', (i) a leader peptide, (ii) anti-CD138 scFv, (iii) a transmembrane domain I, (iv) a costimulatory domain, an activation domain or both, (v) a self-cleaving peptide, (vi) a leader peptide, (vii) anti-CD38 scFv domain, (viii) a transmembrane domain II, and (ix) a costimulatory domain, an activation domain or both.

According to one embodiment, the DNA construct encodes, from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-CD38 scFv domain, (viii) a transmembrane domain II and (ix) an activation domain. According to another embodiment, the DNA construct encodes, from 5' to 3', (i) a leader peptide, (ii) anti-CD38 scFv, (iii) a transmembrane domain II, (iv) an activation domain, (v) a self-cleaving peptide, (vi) a leader peptide, (vii) anti-CD138 scFv domain, (viii) a transmembrane domain I, and (ix) a costimulatory domain.

All definitions and embodiments used in previous aspects, and in particular those related to CARs, their parts and domains as well as to DNA constructs and T-cells are encompassed and embedded herein.

According to one embodiment, the self-cleaving peptide is a peptide having the SEQ ID NO: 26 or an active analog thereof. According to another embodiment, the self-cleaving peptide is IRES peptide or an analog thereof. According to another embodiment, the self-cleaving peptide is encoded by a DNA sequence SEQ ID NO: 27 or a variant thereof.

The terms "variant", "DNA variant", "sequence variant", "polynucleotide variant" and "variant of SEQ ID NO: X" are used herein interchangeably and refer to a DNA polynucleotide having at least 70% sequence identity to the original polynucleotide, wherein X is a number of a sequence. The variant may include mutations such as deletion, addition or substitution such that the mutations do not change the open reading frame and the polynucleotide encodes a peptide or a protein having a substantially similar structure and function as the peptide or a protein encoded by the original polynucleotide. According to some embodiments, the variants are conservative variants. The term "conservative variants" as used herein refers to variants in which a change of one or more nucleotides in a given codon position results in no alteration in the amino acid encoded at that position. Thus, the peptide or the protein encoded by the conservative variants has 100% sequence identity to the peptide or the protein encoded by the original polynucleotide. According to some embodiments, the variant is a non-conservative variant encoding to a peptide or a protein being a conservative analog of the peptide of the protein encoded by the original polynucleotide. According to some embodiments, the variant has at least 75%, at least 80% at least 85%, at least 90%, at least 95%, at least 98% or at least 99% sequence identity to the original polynucleotide.

According to some embodiments, the CARs of the present invention are encoded by two or more different DNA constructs. Thus in some embodiments, the present invention provides a T-cell comprising two different DNA constructs, wherein the first DNA construct comprises a sequence encoding, from 5' to 3', (i) a leader peptide, (ii) anti-CD138 scFv, (iii) a transmembrane domain I (TM-I) and (iv) a costimulatory domain, an activation domain or both, and the second DNA construct comprises a sequence encoding from 5' to 3' (i) a leader peptide, (ii) anti-CD38 scFv domain, (iii) a transmembrane domain II (TM-II) and (iv) a costimulatory domain, an activation domain or both. According to one embodiment, the first DNA construct comprises a sequence encoding, from 5' to 3', (i) a leader peptide, (ii) anti-CD138 scFv, (iii) a TM-I and (iv) a costimulatory domain. According to another embodiment, the second DNA construct comprises a sequence encoding (i) a leader peptide, (ii) anti-CD38 scFv domain, (iii) a TM-II and (iv) an activation domain. According to one embodiment, the first DNA construct comprises a sequence encoding, from 5' to 3', (i) a leader peptide, (ii) anti-CD138 scFv, (iii) a TM-I and (iv) a costimulatory domain and the second DNA construct comprises a sequence encoding (i) a leader peptide, (ii) anti-CD38 scFv domain, (iii) a TM-II and (iv) an activation domain.

According to any one of the above embodiments, either the two CARs are encoded by one or two separate DNA constructs; the leader peptide has the amino acid sequence SEQ ID NO: 20 or an analog thereof. According to another embodiment, the activation domain has the amino acid sequence SEQ ID NO: 23 or an analog thereof. According to a further embodiment, the costimulatory domain has the amino acid sequence SEQ ID NO: 22 or an analog thereof. According to yet another embodiment, the anti-CD138 scFv domain has the amino acid sequence SEQ ID NO: 18 or an analog thereof. According to a certain embodiment, the anti-CD38 scFv domain has the amino acid sequence SEQ ID NO: 19 or an analog thereof. According to some embodiments, TM-I has the amino acid sequence SEQ ID NO: 35. According to a further embodiment, the TM-II has the amino acid sequence SEQ ID NO: 36. According to some embodiments, the leader peptide is encoded by a DNA sequence set forth in SEQ ID NO: 39 or a variant thereof; and/or the anti-CD138 scFv is encoded by a DNA sequence set forth in SEQ ID NO: 28 or a variant thereof; and/or the anti-CD38 scFv is encoded by a DNA sequence set forth in SEQ ID NO: 29 or a variant thereof; and/or the costimulatory domain is encoded by a DNA sequence set forth in SEQ ID NO: 30, or a variant thereof, and/or the activation domain is encoded by a DNA sequence set forth in SEQ ID NO: 31, or a variant thereof. According to some embodiments, the a transmembrane domain I is encoded by the DNA sequence set in SEQ ID NO: 37 or a variant thereof. According to some embodiments, the a transmembrane domain II is encoded by the DNA sequence set in SEQ ID NO: 38 or a variant thereof. According to such embodiments, the analog or the variant has at least 85% sequence identity to the original sequence.

According to other embodiments, the DNA construct encoding both CARs comprises SEQ ID NO: 28. According to other embodiments, such DNA construct comprises a variant, such as conservative variant, of SEQ ID NO: 28.

According to some embodiments, two CARs are encoded by two different DNA construct and the first DNA construct comprises SEQ ID NO: 28. According to other embodiments, the first DNA construct comprises a variant e.g. conservative variant of SEQ ID NO: 28.

According to some embodiments, the DNA construct encoding both CARs comprises SEQ ID NO: 29. According to other embodiments, such DNA construct comprises a variant, such as conservative variant, of SEQ ID NO: 29.

According to some embodiments, two CARs are encoded by two different DNA construct and the second DNA construct comprises DNA sequence SEQ ID NO: 29. According to other embodiments, the second DNA construct comprises a variant e.g. conservative variant of SEQ ID NO: 29.

According to some embodiments, the costimulatory domain is encoded by a DNA sequence set forth in SEQ ID NO: 30 and the activation domain is encoded by a DNA sequence set forth in SEQ ID NO: 31

According to one embodiment, two CARs are encoded by one DNA construct comprising, from 5' to 3, DNA sequences SEQ ID NO: SEQ ID NO: 28, 30, 29 and 31

According to some embodiments, the DNA construct comprises SEQ ID NO: 32 or a variant thereof. According to another embodiment, the DNA construct comprises SEQ ID NO: 33 or a variant thereof. According to another embodiment, the DNA construct comprises from 5' to 3' SEQ ID NO: 32 and SEQ ID NO: 33. According to another embodiment, the DNA construct comprises from 5' to 3' SEQ ID NO: 33 and SEQ ID NO: 32.

According to one embodiment, the present invention provides a T-cell comprising a DNA construct encoding two CARs of the present invention, wherein the DNA construct has SEQ ID NO: 34. According to another embodiment, the DNA construct is a variant, e.g. a conservative variant of SEQ ID NO: 34. According to other embodiments, the variant has at least 90%, at least 95% or at least 98% sequence identity to original sequence.

According to some embodiments, the present invention provides a T-cell comprising two DNA constructs encoding two CARs of the present invention, wherein the first DNA construct comprises the DNA sequence SEQ ID NO: 32 and the second DNA construct comprises the DNA sequence SEQ ID NO: 33. According to one embodiment, the first DNA construct has a DNA sequence being a variant, such as conservative variant of SEQ ID NO: 32. According to one embodiment, the second DNA construct has a DNA sequence being a variant, such as conservative variant of SEQ ID NO: 33. According to a further embodiment, the T-cell comprising two DNA constructs, wherein the first DNA construct comprises the DNA being a variant of SEQ ID NO: 32 and the second DNA construct has a DNA sequence being a variant of SEQ ID NO: 33. According to some embodiments, the variant has at least 85% sequence identity to original sequence. According to other embodiments, the variant has at least 90%, at least 95% or at least 98% sequence identity to original sequence.

According to any one of the above embodiments, the T-cells comprising the DNA constructs of the present invention express or capable of expressing the CARs encoded by the DNA constructs.

The word "expression" or "express" as used herein in reference to a DNA construct means the transcriptional and/or translational product of that construct. The level of expression of a DNA molecule in a cell may be determined on the basis of either the amount of corresponding mRNA that is present within the cell or the amount of protein encoded by that DNA produced by the cell. According to some embodiments, the expression is a conditional expression.

According to a further aspect, the present invention provides a nucleic acid construct encoding two distinct separate chimeric antigen receptors (CARs), wherein the first CAR comprises an antigen binding domain that binds specifically to CD138 and the second CAR comprises an antigen binding domain that binds specifically to CD38. According to one embodiment, nucleic acid construct encodes two distinct separate chimeric antigen receptors wherein the first CAR comprises anti-CD138 scFv and the second CAR comprises anti-CD38 scFv. According to one embodiment, the nucleic acid construct is DNA. Thus in one embodiment, the present invention provides a DNA construct encoding two distinct separate chimeric antigen receptors wherein the first CAR comprises anti-CD138 scFv and the second CAR comprises anti-CD38 scFv.

According to one embodiment, the DNA construct encodes from 5' to 3', (i) a leader peptide, (ii) anti-CD138 scFv, (iii) a transmembrane domain I, (iv) a costimulatory domain, an activation domain or both, (v) a self-cleaving peptide, (vi) a leader peptide, (vii) anti-CD38 scFv domain, (viii) a transmembrane domain II, and (ix) a costimulatory domain, an activation domain or both.

According to one embodiment, the DNA construct encodes, from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-CD38 scFv domain, (viii) a transmembrane domain II and (ix) an activation domain. According to another embodiment, the DNA construct encodes, from 5' to 3', (i) a leader peptide, (ii) anti-CD38 scFv, (iii) a transmembrane domain II, (iv) an activation domain, (v) a self-cleaving peptide, (vi) a leader peptide, (vii) anti-CD138 scFv domain, (viii) a transmembrane domain I, and (ix) a costimulatory domain. According to one embodiment, the leader peptide has the amino acid sequence SEQ ID NO: 20 or an analog thereof. According to another embodiment, the activation domain has the amino acid sequence SEQ ID NO: 23 or an analog thereof. According to a further embodiment, the costimulatory domain has the amino acid sequence SEQ ID NO: 22 or an analog thereof. According to yet another embodiment, the anti-CD138 scFv domain has the amino acid sequence SEQ ID NO: 18 or an analog thereof. According to a certain embodiment, the anti-CD38 scFv domain has the amino acid sequence SEQ ID NO: 19 or an analog thereof. According to some embodiments, TM-I has the amino acid sequence SEQ ID NO: 35. According to a further embodiment, the TM-II has the amino acid sequence SEQ ID NO: 36.

According to some embodiments, the leader peptide is encoded by a DNA sequence set forth in SEQ ID NO: 39 or a variant thereof. According to other embodiments, the anti-CD138 scFv is encoded by a DNA sequence set forth in SEQ ID NO: 28 or a variant thereof. According to some embodiments, the anti-CD38 scFv is encoded by a DNA sequence set forth in SEQ ID NO: 29 or a variant thereof. According to some embodiments, the costimulatory domain is encoded by a DNA sequence set forth in SEQ ID NO: 30, or a variant thereof. According to yet another embodiment, the activation domain is encoded by a DNA sequence set forth in SEQ ID NO: 31 or a variant thereof. According to some embodiments, the costimulatory domain is encoded by a DNA sequence SEQ ID NO: 30 and the activation domain is encoded by a DNA sequence SEQ ID NO: 31. According to some embodiments, the self-cleaving peptide is encoded by DNA sequence SEQ ID NO: 27 or a variant thereof. According to some embodiments, the transmembrane domain I is encoded by the DNA sequence set in SEQ ID NO: 37 or a variant thereof. According to some embodiments, the transmembrane domain II is encoded by the DNA sequence set in SEQ ID NO: 38 or a variant thereof.

According to one embodiment, the DNA construct comprises, from 5' to 3, DNA sequences SEQ ID NO: SEQ ID NO: 28, 30, 29 and 31.

According to some embodiments, the DNA construct comprises SEQ ID NO: 32 or a variant thereof. According to another embodiment, the DNA construct comprises SEQ ID NO: 33 or a variant thereof. According to another embodiment, the DNA construct comprises from 5' to 3' SEQ ID NO: 32 and SEQ ID NO: 33. According to another embodiment, the DNA construct comprises from 5' to 3' SEQ ID NO: 33 and SEQ ID NO: 32. According to some embodiments, the DNA construct comprises a self-cleaving sequence having DNA sequence SEQ ID NO: 27 between sequences SEQ ID NO: 32 and SEQ ID NO: 33.

According to some embodiments, the present invention provides a nucleic acid construct comprising SEQ ID NO: 34. According to some embodiments, the present invention provides a nucleic acid construct consisting of SEQ ID NO: 34. According to another embodiment, the DNA construct is a variant, e.g. a conservative variant of SEQ ID NO: 34.

According to some embodiments, the DNA construct is operably linked to a promoter. The term "promoter" as used herein refers to a regulatory sequence that initiates transcription of a downstream nucleic acid. The term "promoter" refers to a DNA sequence within a larger DNA sequence defining a site to which RNA polymerase may bind and initiate transcription. A promoter may include optional distal enhancer or repressor elements. The promoter may be either homologous, i.e., occurring naturally to direct the expression of the desired nucleic acid, or heterologous, i.e., occurring naturally to direct the expression of a nucleic acid derived from a gene other than the desired nucleic acid. A promoter may be constitutive or inducible. A constitutive promoter is a promoter that is active under most environmental and developmental conditions. An inducible promoter is a promoter that is active under environmental or developmental regulation. Promoters may be derived in their entirety from a native gene, may comprise a segment or fragment of a native gene, or may be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. It is further understood that the same promoter may be differentially expressed in different tissues and/or differentially expressed under different conditions.

According to another aspect, the present invention provides a vector comprising the nucleic acid construct of the present invention. According to one embodiment, the a DNA construct encodes two distinct separate chimeric antigen receptors wherein the first CAR comprises anti-CD138 scFv and the second CAR comprises anti-CD38 scFv. According to another embodiment, the vector comprises a DNA construct encoding from 5' to 3', (i) a leader peptide, (ii) anti-CD138 scFv, (iii) a transmembrane domain I, (iv) a costimulatory domain, an activation domain or both, (v) a self-cleaving peptide, (vi) a leader peptide, (vii) anti-CD38 scFv domain, (viii) a transmembrane domain II, and (ix) a costimulatory domain, an activation domain or both. According to some embodiments, the DNA construct comprising, from 5' to 3, DNA sequences SEQ ID NO: SEQ ID NO: 28, 30, 29 and 31. According to another embodiment, the DNA construct comprises from SEQ ID NO: 32 and SEQ ID NO: 33. According to some embodiments, the DNA construct comprises sequence SEQ ID NO: 27 between sequences SEQ ID NO: 32 and SEQ ID NO: 33. According to yet another embodiment, the present invention provides a vector comprising DNA construct comprising SEQ ID NO: 34. According to a further embodiment, the present invention provides a vector comprising DNA construct consisting of SEQ ID NO: 34.

The terms "vector" and "expression vector" are used herein interchangeably and refer to any viral or non-viral vector such as plasmid, virus, retrovirus, bacteriophage, cosmid, artificial chromosome (bacterial or yeast), phage, binary vector in double or single stranded linear or circular form, or nucleic acid, sequence which is able to transform host cells and optionally capable of replicating in a host cell. The vector may be integrated into the cellular genome or may exist extrachromosomally (e.g., autonomous replicating plasmid with an origin of replication). The vector may contain an optional marker suitable for use in the identification of transformed cells, e.g., tetracycline resistance or ampicillin resistance. A cloning vector may or may not possess the features necessary for it to operate as an expression vector.

According to other embodiments, the vector is a virus, e.g. a modified or engineered virus. The modification of a vector may include mutations, such as deletion or insertion mutation, gene deletion or gene inclusion. In particular, a mutation may be done in one or more regions of the viral genome. Such mutations may be introduced in a region related to internal structural proteins, replication, or reverse transcription function. Other examples of vector modification are deletion of certain genes constituting the native infectious vector such as genes related to the virus' pathogenicity and/or to its ability to replicate.

According to one embodiment, the vector is a viral vector. Any virus can be used by the methods disclosed herein. The virus can be a dsDNA virus (e.g. Adenoviruses, Herpesviruses, Poxviruses), a single stranded "plus" sense DNA virus (e.g., Parvoviruses) a double stranded RNA virus (e.g., Reoviruses), a single stranded sense RNA virus (e.g. Picornaviruses, Togaviruses), a single stranded "minus" sense RNA virus (e.g. Orthomyxoviruses, Rhabdoviruses), a single stranded sense RNA virus with a DNA intermediate (e.g. Retroviruses), or a double stranded reverse transcribing virus (e.g. Hepadnaviruses). In certain non-limiting embodiments of the present invention, the virus is poliovirus (PV), rhinovirus, influenza virus including avian flu (e.g. H5N1 subtype of influenza A virus), severe acute respiratory syndrome (SARS) coronavirus, Human Immunodeficiency Virus (HIV), Hepatitis B Virus (HBV), Hepatitis C Virus (HCV), infectious bronchitis virus, ebolavirus, Marburg virus, dengue fever virus (Flavivirus serotypes), West Nile disease virus, Epstein-Barr virus (EBV), yellow fever virus, Ebola (ebolavirus), chickenpox (varicella-zoster virus), measles (a paramyxovirus), mumps (a paramyxovirus), rabies (Lyssavirus), human papillomavirus, Kaposi's sarcoma-associated herpesvirus, Herpes Simplex Virus (HSV Type 1), or genital herpes (HSV Type 2). According to some embodiments, the vector is a virus selected from lentivirus, adenovirus, modified adenovirus and retrovirus. In one particular embodiment, the vector is lentivirus. According to any one of the above embodiments, the virus is a non-pathogenic virus or a modified virus lacking pathogenic genes.

According to another aspect, the present invention provides a cell comprising the DNA construct or the vector of the present invention. According to some embodiments, the cell is prokaryotic or eukaryotic cells. According to another embodiment, the cell is non-human or human mammal cell. According to some embodiments, the cell is human cell. According to some particular embodiment, the cell is T-cell. According to one embodiment, the T-cell is selected from CD4+ T-cell and a CD8+ T-cell.

According to another aspect, the present invention provides a pharmaceutical composition comprising a plurality of the T-cells of the present invention and a pharmaceutically acceptable carrier.

All definitions and embodiments used in previous aspects, and in particular those related to CARs, their parts and domains as well as to DNA constructs and T-cells are encompassed and embedded herein.

The term "pharmaceutical composition" as used herein refers to a composition comprising the T-cells of the present invention formulated together with one or more pharmaceutically acceptable carriers.

Formulation of the pharmaceutical composition may be adjusted according to applications. In particular, the pharmaceutical composition may be formulated using a method known in the art so as to provide rapid, continuous or delayed release of the active ingredient after administration to mammals. For example, the formulation may be any one selected from among plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, capsules, creams, troches, tinctures, pastes, pills, and soft or hard gelatin capsules. According to one embodiment, the composition is formulated as a liquid formulation. According to another embodiment, the composition is formulated as a solution for injection.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain other active compounds providing supplemental, additional, or enhanced therapeutic functions.

The terms "pharmaceutically acceptable" and "pharmacologically acceptable" include molecular entities and compositions that do not produce an adverse, allergic, or other untoward reactions when administered to an animal, or human, as appropriate. For human administration, preparations should meet sterility, pyrogenicity, general safety, and purity standards as required by a government drug regulatory agency, e.g., the United States Food and Drug Administration (FDA) Office of Biologics standards.

The composition of the present invention may be administered by any known method. The terms "administering" or "administration of" a composition to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. According to one embodiments, the pharmaceutical composition is administered parenterally, i.e. not orally. According to one embodiments, the pharmaceutical composition is administered systemically. According to another embodiment, the pharmaceutical composition is administered locally. According to one embodiments, the pharmaceutical composition is administered intravenously. According to another embodiment, the pharmaceutical composition is administered intramuscularly.

According to another embodiment, the pharmaceutical composition comprises a plurality of T-cell comprising the DNA construct of the present invention. According to one embodiment, the T-cell comprises one construct encoding the two CARs of the present invention. According to another embodiment, the T-cell comprises two constructs, each encoding one separate CAR of the present invention.

According to one embodiment, the pharmaceutical comparison comprises a plurality of T-cell genetically modified to express at least two distinct separate chimeric antigen receptors (CARs), wherein the first CAR comprises an anti-CD138 scFv and the second CAR comprises anti-CD38 scFv. According to some embodiments, the T cells are selected are from CD4+ T-cells, CD8+ T-cell or combination thereof. Thus, in one embodiment, the present invention provides a pharmaceutical composition comprising CD4+ T-cells genetically modified to express two distinct separate CARs, wherein the first CAR comprises anti-CD138 scFv and the second CAR comprises anti-CD38 scFv. According to another embodiment, the present invention provides a pharmaceutical composition comprising CD8+ T-cells genetically modified to express two distinct separate CARs, wherein the first CAR comprises anti-CD138 scFv and the second CAR comprises anti-CD38 scFv. According to some such embodiments, the first CAR comprises amino acid sequences SEQ ID NO: 18 and SEQ ID NO: 22. According to another embodiment, the second CAR comprises amino acid sequences SEQ ID NO: 19 and SEQ ID NO: 23. According to one embodiment, the first CAR comprises amino acid sequences SEQ ID NO: 18 and SEQ ID NO: 22 and the second CAR comprises amino acid sequences SEQ ID NO: 19 and SEQ ID NO: 23. According to one such embodiments, the first CAR has the amino acid sequence SEQ ID NO: 24 or being an analog thereof and the second CAR has the amino acid sequence SEQ ID NO: 25 or being an analog thereof. According to a further embodiment, the present invention provides a pharmaceutical composition comprising CD4+ and/or CD8+ T-cells genetically modified to express two distinct separate CARs, wherein the first CAR consists of amino acid sequence SEQ ID NO: 24 and the second CAR consists of amino acid sequence SEQ ID NO: 25. According to some embodiments, the T-cells are capable of expressing the CARs. According to another embodiment, the T-cells express the CARs.

According to one embodiment, the pharmaceutical composition comprises T-cells comprising the DNA construct of the present invention. According to another embodiment, the DNA construct encoding from 5' to 3', (i) a leader peptide, (ii) anti-CD138 scFv, (iii) a transmembrane domain I, (iv) a costimulatory domain, an activation domain or both, (v) a self-cleaving peptide, (vi) a leader peptide, (vii) anti-CD38 scFv domain, (viii) a transmembrane domain II, and (ix) a costimulatory domain, an activation domain or both. According to some embodiments, the DNA construct comprising, from 5' to 3, DNA sequences SEQ ID NO: SEQ ID NO: 28, 30, 29 and 31. According to another embodiment, the DNA construct comprises from SEQ ID NO: 32 and SEQ ID NO: 33. According to some embodiments, the DNA construct comprises sequence SEQ ID NO: 27 between sequences SEQ ID NO: 32 and SEQ ID NO: 33. According to yet another embodiment, the present invention provides a vector comprising DNA construct comprising SEQ ID NO: 34. According to a further embodiment, the present invention provides a vector comprising DNA construct consisting of SEQ ID NO: 34.

According to any one of the above embodiments, the pharmaceutical composition of for use in treating cancer.

The term "treating" a condition or patient as used herein refers to taking steps to obtain beneficial or desired results, including clinical results. Beneficial or desired clinical results include, but are not limited to, or ameliorating abrogating, substantially inhibiting, slowing or reversing the progression of a cancer substantially ameliorating or alleviating clinical or esthetical symptoms of a condition, substantially preventing the appearance of clinical symptoms of a disease, condition, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and/or (e) limiting recurrence of symptoms in patients that were previously asymptomatic for the disorder(s).

According to one embodiment, the cancer is myeloma. According to another embodiment, the cancer is multiple myeloma.

The term "myeloma" refers to a cancer of bone marrow. The term "multiple myeloma" refers to a cancer of plasma white blood cells.

Thus, in some embodiments, the present invention provides a pharmaceutical composition comprising a plurality of T-cells genetically modified to express two distinct separate CARs, wherein the first CAR anti-CD138 scFv and the second CAR comprises anti-CD38 scFv, for use in treating multiple myeloma. In certain embodiments, such pharmaceutical composition is for use in treating multiple myeloma. In one embodiment, the T cells are CD4+ T-cells or CD8+ T-cells genetically modified to express two distinct separate CARs. According to some such embodiments, the first CAR comprises amino acid sequences SEQ ID NO: 18 and SEQ ID NO: 22. According to another embodiment, the second CAR comprises amino acid sequences SEQ ID NO: 19 and SEQ ID NO: 23. According to one embodiment, the first CAR comprises amino acid sequences SEQ ID NO: 18 and SEQ ID NO: 22 and the second CAR comprises amino acid sequences SEQ ID NO: 19 and SEQ ID NO: 23. According to one such embodiments, the first CAR has the amino acid sequence SEQ ID NO: 24 or being an analog thereof and the second CAR has the amino acid sequence SEQ ID NO: 25 or being an analog thereof. According to a further embodiment, the present invention provides CD4+ and/or CD8+ T-cells genetically modified to express two distinct separate CARs, wherein the first CAR consists of amino acid sequence SEQ ID NO: 24 and the second CAR consists of amino acid sequence SEQ ID NO: 25. According to any one of the above embodiments, the T-cell expressed the two CARs.

According to any one of the above aspects, the term treating encompasses increasing survival rate by at least 1.5, 2, 2.5 or 3 folds. According to another embodiment, treating comprises reducing side effects in comparison to traditional treatment or in comparison to treatment with T cells expressing one CAR.

According to some embodiments, the treating using the pharmaceutical composition has much lower rate of adverse effects.

According to another aspect, the present invention provides a method of treating cancer in a subject in need thereof, comprising administering an effective amount of T-cells of the present invention. According to another embodiment, the method comprises administering the pharmaceutical composition comprising the T-cells of the present invention. According to one embodiment, the cancer is myeloma. According to another embodiment, the cancer is multiple myeloma.

According to yet another aspect, the present invention provides a use of T-cells genetically modified to express at least two distinct separate chimeric antigen receptors (CARs) for preparation of a medicament for treating cancer in a subject in need thereof, wherein the wherein the first CAR comprises an antigen binding domain that binds specifically to CD138 and the second CAR comprises an antigen binding domain that binds specifically to CD38. According to one embodiment, the T-cell comprise the DNA construct of the present invention. According to another embodiment, the T-cell comprises at least two DNA construct, encoding separately to a CAR comprising an antigen binding domain that binds specifically to CD138 and to a CAR comprising an antigen binding domain that binds specifically to CD38.

According to another aspect, the present invention provides a method of preparation of T-cells of the present invention. According to one embodiment, the present invention provides a method of preparation of T-cells genetically modified to express at least two distinct separate chimeric antigen receptors (CARs), wherein the first CAR comprises an antigen binding domain that binds specifically to CD138 and the second CAR comprises an antigen binding domain that binds specifically to CD38, said method comprises transfecting of T-cells with the DNA construct of the present invention.

All definitions and embodiments used in previous aspects, and in particular those related to CARs, their parts and domains as well as to DNA constructs and T-cells are encompassed and embedded herein.

The terms "transfection", "transduction", "transfecting" or "transducing" can be used interchangeably and are defined as a process of introducing a nucleic acid molecule to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art.

According to one embodiment, the T-cells are CD4+ T-cells. According to another embodiment, the T-cells are CD8+ cells.

According to one embodiment, the method comprises transducing T cells with at least one DNA construct encoding two CARs, wherein the construct comprises, from 5' to 3, DNA sequences SEQ ID NOs:28, 30, 29 and 31. According to some embodiments, the DNA construct comprises SEQ ID NO: 32 or a variant thereof. According to another embodiment, the DNA construct comprises SEQ ID NO: 33 or a variant thereof. According to another embodiment, the DNA construct comprises from 5' to 3' SEQ ID NO: 32 and SEQ ID NO: 33. According to another embodiment, the DNA construct comprises from 5' to 3' SEQ ID NO: 33 and SEQ ID NO: 32.

According to one embodiment, a DNA construct encoding two CARs of the present invention has SEQ ID NO: 34. According to another embodiment, the DNA construct is a variant, e.g. a conservative variant, of SEQ ID NO: 34.

According to one embodiment, the method comprises transducing T cells with two DNA constructs each encoding one separate CAR of the present invention, wherein the first DNA construct comprises the DNA sequence set forth in SEQ ID NO: 32 and the second DNA construct comprises the DNA sequence set forth in SEQ ID NO: 33. According to one embodiment, the first DNA construct has a DNA sequence being a variant, such as conservative variant of SEQ ID NO: 32. According to one embodiment, the second DNA construct has a DNA sequence being a variant, such as conservative variant of SEQ ID NO: 33. According to a further embodiment, the T-cell comprising two DNA constructs, wherein the first DNA construct comprises the DNA being a variant of SEQ ID NO: 32 and the second DNA construct has a DNA sequence being a variant of SEQ ID NO: 33.

According to any one of the above embodiments, the transduction is performed using a viral vector selected from retroviral, adenoviral, lentiviral and adeno-associated viral vectors.

According to some embodiments, the vector may contain an optional marker suitable for use in the identification of transformed cells.

The terms "comprising", "comprise(s)", "include(s)", "having", "has" and "contain(s)," are used herein interchangeably and have the meaning of "consisting at least in part of". When interpreting each statement in this specification that includes the term "comprising", features other than that or those prefaced by the term may also be present. Related terms such as "comprise" and "comprises" are to be interpreted in the same manner. The terms "have", "has", having" and "comprising" may also encompass the meaning of "consisting of" and "consisting essentially of", and may be substituted by these terms. The term "consisting of" excludes any component, step or procedure not specifically delineated or listed. The term "consisting essentially of" means that the composition or component may include additional ingredients, but only if the additional ingredients do not materially alter the basic and novel characteristics of the claimed compositions or methods.

Having now generally described the invention, the same will be more readily understood through reference to the following examples, which are provided by way of illustration and are not intended to be limiting of the present invention.

EXAMPLES

Materials and Methods
Cell Lines and Culture

Cell lines (CAG/CAG-Luciferase expressing human multiple myeloma cell line, and PC-3, a human prostate cancer cell line) were cultured in RPMI (Biological industries, Bet-Ha'emek, Israel), supplemented with 10% fetal calf serum (FCS) (Hy clone) and 2 mM glutamine, in a humidified 37° C. incubator with 5% $CO_2$. 293T human embryonic cells (ATCC) and PG13 (a murine cell line expressing Gag-Pol and infected with pCL-Ampho viral envelope protein) were cultured in DMEM supplemented with 10% FCS, 2 mM glutamine and 1 mM sodium pyruvate. The cells were incubated in a humidified 37° incubator with 7.5% $CO_2$. Human lymphocytes were cultured in RPMI-1640 supplemented with 10% FCS and 50 µM 2-mercaptoethanol, and incubated in a humidified 37° incubator with 5% $CO_2$. All media were supplemented with a mixed antibiotic solution containing penicillin (100 U/ml), streptomycin (100 µg/ml) and neomycin (10 µg/ml) (Bio-Lab, Jerusalem, Israel). All cells were checked for *mycoplasma* using PCR. The cells were frozen at low passage, and the number of passages after thawing was recorded. Cells were maintained in culture for not longer than 4 weeks, which corresponds to approximately 12 passages. Primary cell lines that were used in this project were ordered from Cell Biologics and Lonzo from Almog and Eisenberg Bros. Ltd. Each primary cell was propagated as indicated in its data sheet.

Antibodies and Reagents

Purified anti-human CD3 was prepared in-house from the hybridoma OKT3. Purified anti-human CD28 was purchased from Southern Biotechnology Associates, Inc (Birmingham, USA). Human IL-2 was purchased from Novartis-Pharma (England). Recombinant, His or Human Fc-tagged CD38 and CD138 proteins were purchased from Sino Biological. Anti-His antibodies were purchased from Abcam; anti-human Fc (γ-specific) antibodies were purchased from eBioscience. Anti-human CD3 APC was obtained from BioLegend. Anti-human CD38 PE-cy7, anti-human CD-138 APC, and anti-human ErbB2 FITC were purchased from eBioscince.

Example 1

In the following example, human T cells, transduced with different chimeric antigen receptors were prepared and tested. The aim of present example was to test the efficacy of T-cells transduces with two different CARs specifically binding to two distinct antigens that are clinically relevant for treatments of multiple myeloma (MM). For this purpose two clinically relevant antigens were chosen: CD38 and CD138. Two CARs aimed at specifically binding these antigens were generated. One CAR comprised scFv derived from anti-CD138-specific monoclonal antibody with $V_L$ and $V_H$ having the sequences SEQ ID NO: 13 and SEQ ID NO: 14, respectively. The second CAR comprises scFv derived from anti-CD38-specific monoclonal antibody with $V_L$ and $V_H$ having the sequences SEQ ID NO: 15 and SEQ ID NO: 16, respectively. The $V_L$ and $V_H$ in each one of the CARs was connected with 14 amino acid linker having the sequence GSTSGSGKSSEGKG (SEQ ID NO: 17).

The test item of the present experiments were T-cells transduced with two following CARs: one having anti-CD138 (αCD138) scFv and one having anti-CD38 (αCD38) scFv. In order to reduce "on target off tumor" toxicity, the costimulatory domain and activation signaling elements were separated between the two CARs; a CAR having αCD138 scFv harbored only a costimulatory domain (a transmembrane and co-stimulatory domain of CD28 have the sequence SEQ ID NO: 35 and SEQ ID NO: 22, respectively) and the CAR having αCD38 scFv had the activation signaling element only (the transmembrane domain of CD8 and an FcR-gamma domain have the sequence SEQ ID NO: 36 and SEQ ID NO: 26, respectively). The two CARs were placed in one DNA construct comprising a self-cleaving peptide T2A, having the sequence SEQ ID NO: 26, between them. The schematic presentation of the construct is shown in FIG. 1, and the used construct had the sequence SEQ ID NO: 21. The construct is referred as Dual-CAR.

Several control T-cell comprising different CARs were used. Switch refers to a control comprising two CARs in which one of the clinically relevant CARs, i.e. anti-CD138 CAR or anti-CD38 CAR was replaced with anti-ErbB2 CAR (N29, ErbB2 is not expressed in multiple myeloma) The following clones were used to generate the modified T-cells:

αCD138-CD28-γ
αCD38-CD28-γ
Dual-CAR: αCD138-CD28-T2A-αCD38-γ
Switch 1 (control 1): N29-CD28-T2A-αCD38-γ
Switch 2 (control 2): αCD138-CD28-T2A-N29-γ in which αCD138 is an anti CD138 scFv; αCD38 is an anti CD38 scFv; γ—FcRγ activation domain (immunoreceptor tyrosine-based activation motif—ITAM); CD28—costimulatory element of CD28; T2A—self-cleaving peptide and N29—anti-ErbB2 scFv.

First, the ability of T cells to undergo transduction with the CARs using virus derived from the packaging cells was tested. Human peripheral blood lymphocytes (PBLs) were activated for 48 hours, and transduced with supernatant from the relevant packaging cell line. After two days from transduction, cells were stained for protein expression and analyzed by FACS.

T-Cell Transduction

Briefly, peripheral blood lymphocytes (PBL) from healthy human donors were isolated by centrifugation through a Lymphoprep gradient (Axis-shield, Oslo, Norway) and cultured at $3 \times 10^6$ cells/well in 4 mL complete RPMI-1640 supplemented with 50 µM 2-mercaptoethanol. Cells were stimulated for 2 days on non-tissue culture-treated 6-well plates (Falcon) pre-coated with both 1 µg/ml anti-CD3 and rat anti-human CD28 (AbD Serotec, USA) antibodies. Activated lymphocytes were then harvested by vigorous flushing with PBS. Cells were pelleted by centrifugation, and resuspended in viral supernatant at a density of $2-3 \times 10^6$ cells/ml. Cells (1.5 ml) were then added to wells of non-tissue culture-treated 6-well plates (Falcon) pre-coated with RetroNectin™ (12 µg/ml, 4 ml/well, Takara Shuzu Ltd. Otsu, Japan). Following 6 h incubation at 37° C., 7.5% $CO_2$, the viral supernatant was gently removed and replaced with lymphocyte medium supplemented with IL-2 (100 IU/ml), and incubated overnight at 37° C., 5% $CO_2$.

The transduction procedure was repeated on the next day. On the day following the second infection, lymphocytes were harvested by vigorous flushing and washing of the plates with PBS. The cells were re-suspended in lymphocyte medium supplemented with 350 IU/ml of IL-2, and incubated at 37° C., 5% $CO_2$.

Figure 2:
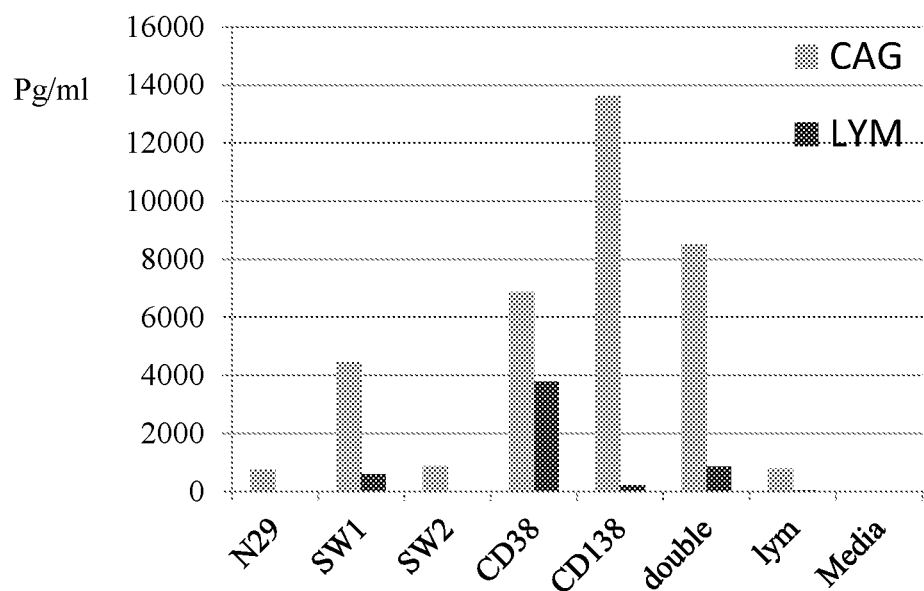
FIG. 2 shows the ability of T-cells transduced with different CAR constructs to interact with CAG cell line expressing CD38 and CD138, as tested by IFN-γ assay. The figure is a representative out of 4 repeats; the figure shows secretion of IFN-γ implying there is a stimulation of different transduced T-cells as marked in the figure.

The ability of T-cells transduced with different constructs to undergo specific stimulation by CAG cell line expressing CD38 and CD138 antigens was tested using INF-γ assay the CAG cell line. The results, shown as a concentration of IFN-γ are presented in FIG. 2. The figure shows representative results of one out of 4 repeats. Secretion of IFN-γ by the transduced T-cells is among others predefined by the level of transduction. As can be seen from this figure, the T-cells transduced with different CARs stimulated IFN-γ secretion. The ratio of transduction of CAR T cell is different between repeats, thus the essence of the figure is to show that the CARs are stimulated, and the dual CAR has an impressive stimulation.

Results

First of all it can be seen that T-cells transduced with different CARs aiming different antigens are responsive to cells expressing the corresponding antigens. We compared the ability of T-cells transduced with a dual-CAR-αCD138-CD28-αCD38-γ to selectively respond to CAG cells expressing both CD38 and CD138. Jurkat cells, which express CD38 only, served as a control for that purpose. As can be seen form FIG. 2, under the experimental conditions the presence of αCD38-γ CAR in T-cells was sufficient to endow the T-cells with full activation capacity independently of costimulation. This is easily concluded from the results showing that T-cells expressing N29-CD28-T2A-αCD38-γ (switch 1) or αCD38 CARs demonstrated high IFN-γ secretion upon incubation with jurkat cells.

The relatively high signal seen for T-cells expressing αCD38 CAR upon incubation with medium may be explained by interactions of the αCD38 CAR with the transduced T-cell which are naturally express CD38 antigen.

Example 2

Figure 3A:
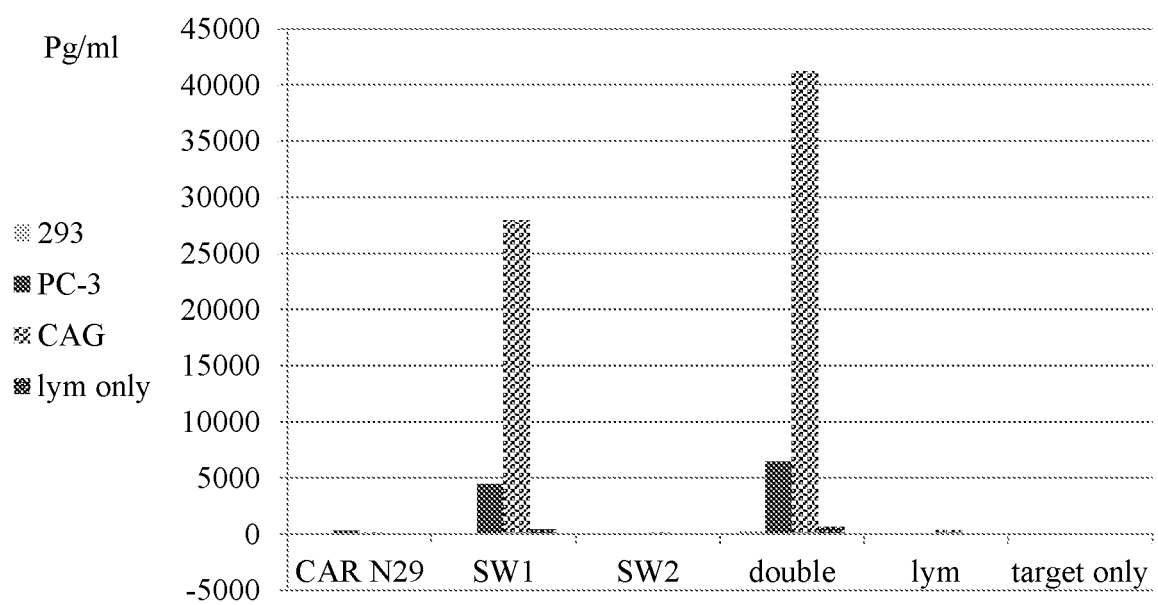
FIG. 3A—stimulation by different cell lines.

In an experimental arrangement similar to that described in Example 1, IFN-γ secretion by T-cells transduced with CAR-N29, switch 1 switch 2, or Dual-CAR (αCD138-CD28-T2A-αCD38) upon incubation with different cell lines was measured. The cell lines were 293—control cell line (that do not express CD38, ErbB2 or CD138), CAG, PC-3—(prostate cancer cell line having low expression of CD38) and incubation of lymphocytes without target cells (only media). The results are presented in FIG. 3A It can be seen from the results that both SW1 and Dual-CAR have low secretion of IFN-γ upon incubation with PC-3 cells. This implies that although some reaction of T-cells transduced with Dual-CAR may be expected, it is substantially lower that the reaction with cells profoundly expressing CD38. It can be also seen that the effect of Dual-CAR is much higher than that of SW1. This was completely unexpected considering that SW2 did not show any IFN-γ secretion. In an additional experiment, in order to show the safety of the double CAR, we have looked in to the stimulation against normal cells.

Figure 3B:
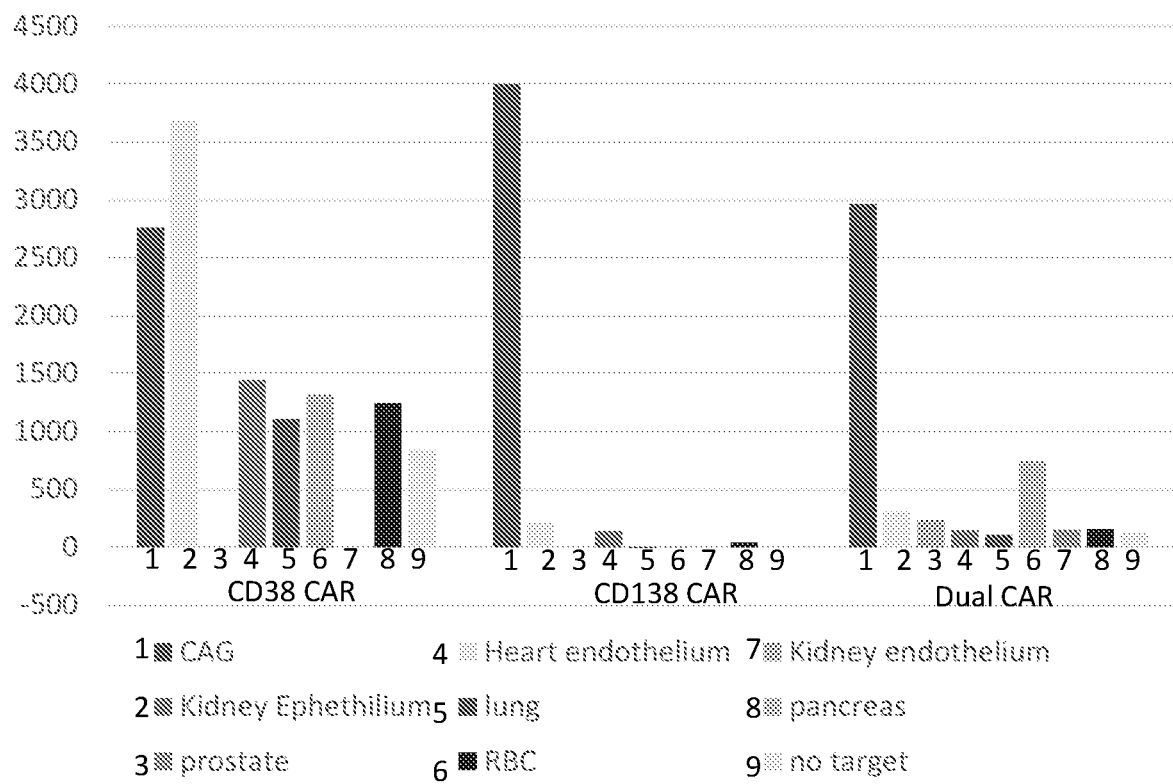
FIG. 3B—comparison of the activity of CAR T-cells toward normal primary tissues. The result are expressed as concentration of IFN-γ in pg/ml (ELISA).

To further analyze the potential toxicity of each single or dual CAR against normal tissues, and predict the expected 'off-tumor on-target' effect, different CARs were stimulated using normal primary human tissues. The results are presented in FIG. 3B. Seven different primary cells as indicated originating from healthy human donors, with CD38/CD138-CD28-γ or dual CAR. The CD38 single CAR showed stronger stimulation by several normal tissues compared to the dual CAR. The dual CAR showed reduced reactivity against the tested cells relative to the CD38 single CAR. Surprisingly, the CD138 CAR did not show any IFN-γ secretion against the analyzed tissues even though it is known to be expressed on many tissue types (protein atlas).

Figure 4:
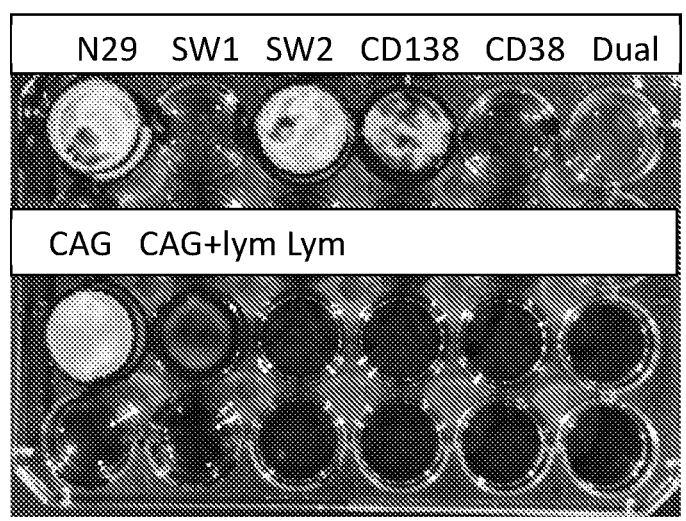
FIG. 4 shows killing of CAG-LUC cells by dual CAR T cells. Luciferase-expressing CAG cells were incubated with transduced CAR T cells

In order to demonstrate the relationship between IFN-γ secretion and target cell killing by the CAR T cells, we stimulated the CAR T cells using stable luciferase-infected CAG cells at a ratio of 1:2 (target:effector CAR), and after 20 hours of incubation, we analyzed the cultures by bioluminescence imaging (IVIS). As shown in FIG. 4, the specific and efficient killing of the dual CAR compared to the controls. CD138-CD28-γ CAR shows a lower extent of killing compared to the dual CAR T cell. The control of SW1 consistently shows efficient killing despite activating only one signal (as only CD38 is expressed on the CAG cells), without the full two signal activation. Furthermore, the CD38 full CAR shows killing effectiveness, as well. However, with dual antigen recognition, clearance of the CAG cell line was observed, as well as better IFN-γ secretion.

Example 3. In Vivo Efficacy of Dual CAR

Materials and Methods

We have calibrated the in-vivo human multiple myeloma (MM) model, which is based on the MM cell line CAG on the immunodeficient mouse strain NOD scid-gamma (NSG). These mice lack mature lymphocytes and are deficient in multiple cytokine signaling pathways, thereby allowing the engraftment of a wide range of human cells and tissues. We first determined the optimal number of injected MM cells, the route of administration and the effect of preconditioning of recipient mice for obtaining a convenient window for CAR T cell treatment (data not shown). It was determined that IV injection of $10^6$ of CAG MM cells followed by irradiated in 200 RAD on day 7 allowed efficient development of the tumor and provided the desired tumor model.

Thus, about $10^6$ of CAG MM cells were injected to mice (denoted as Day 0). At Day 7 the mice were irradiated in 200 RAD (which did not affect tumor growth) and at Day 8, about $10^7$ of modified T-cell transduced with different CARs were IV injected.

Tissues from mice treated with different CAR T-cells were taken at day 25 and analyzed by histology with anti CD138 staining and by FACS (data not shown). The results of the histological are presented in FIG. 5.

Further we evaluated the anti-MM activity of T-cells transduced with the Dual-CAR, switch 1, switch 2 or single CARs in comparison to untreated mice followed from survival curves. The results are presented in FIG. 6.

Results

Figure 5:
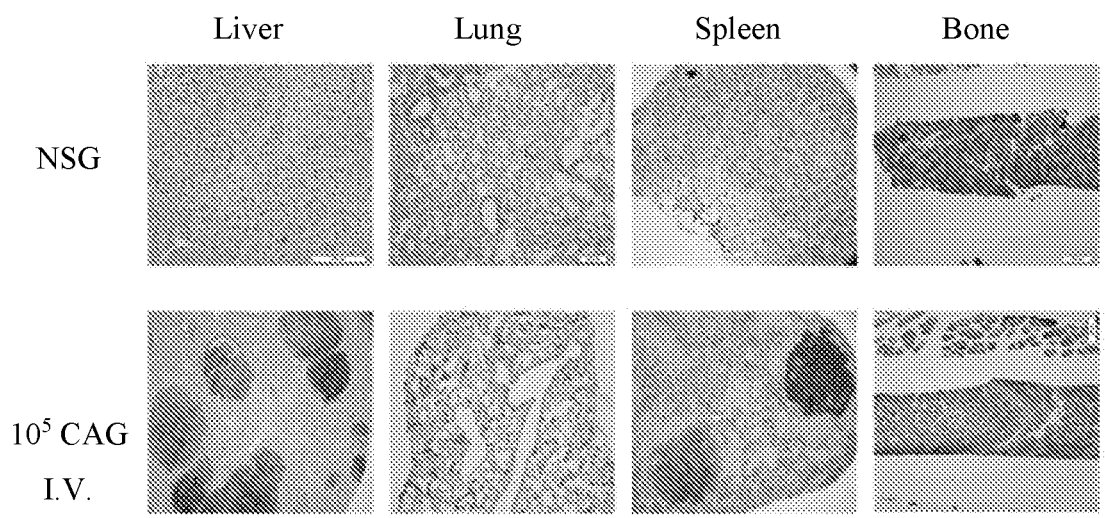
FIG. 5 shows images of anti-human CD138 immunohistology of tissues from NSG mice transplanted with human CAG multiple myeloma cell line vs control.

It can be seen from FIG. 5 that following injection of CAG MM cells, tumor lesions were found in all tested tissues, i.e. in liver, lung, spleen and bone.

Figure 6:
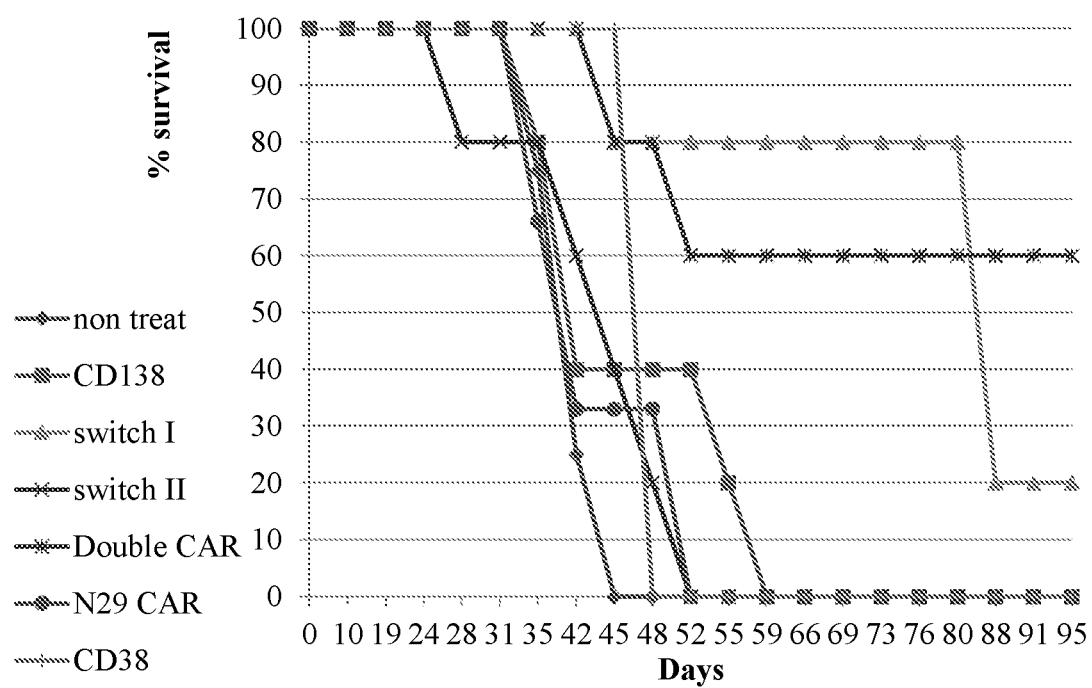
FIG. 6 shows the survival curve of mice injected with CAG multiple myeloma cell and treated with T-cell transduced with different CAR constructs.

When searching the CARs by FACS, records lymphocytes found in the blood of treated NSG mice 26 days post-injection of CAG (data not shown). This clearly indicate that the transduced T-cells comprising the therapeutic dual CAR has lasted at least 26 days in the blood. As can be clearly seen from FIG. 6 showing the survival curves of mice treated with T-cells transduced with different CARs, mice of all groups, except for those treated with Dual-CAR or αCD38 CAR, died in average after 40-45 days following CAG MM cells injection from loss of weight due to graft-versus-host condition as well as from the tumor itself as can be seen in the control untreated group. The T-cells transduced with αCD38 CAR showed a significant therapeutic effect, however, eventually only 20% of mice survived after 85 day. Mice treated with Dual-CAR T-cells showed significantly better survival rate in comparison to those treated with CD38 CAR-T cells with 60% survival after more than 95 days. Mice were sacrificed on day to allow histology and FACS analysis and not because of their tumor load.

Figure 7:
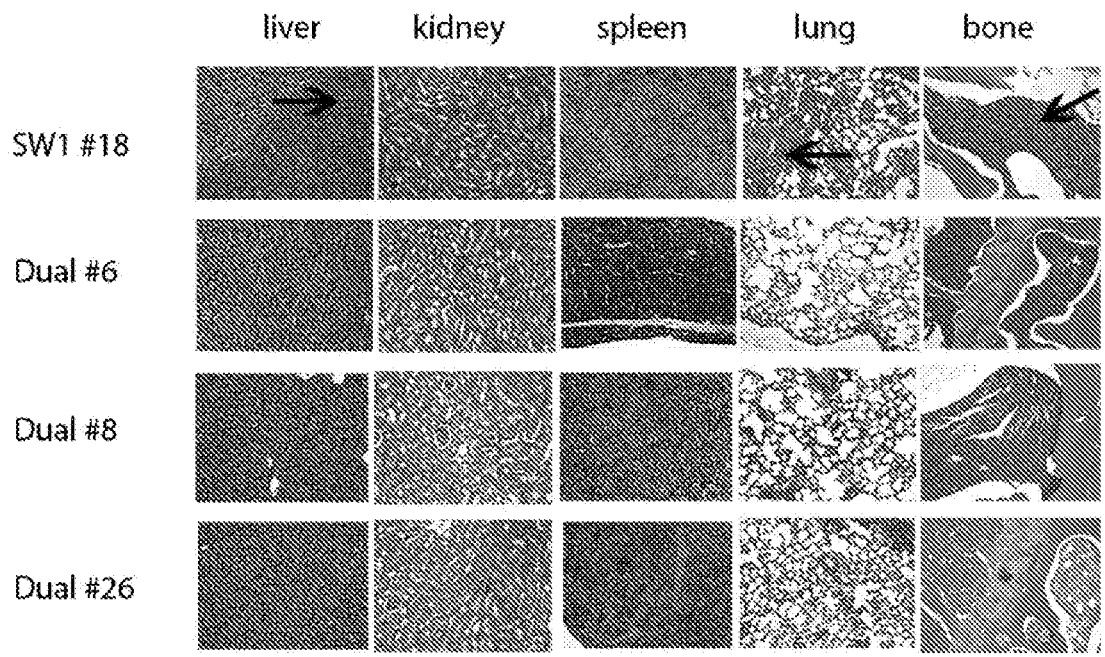
FIG. 7 Hematoxylin and eosin (H&E) staining of tissues from surviving mice transplanted with CAG cell line and treated with SW1 or dual CAR.

All three dual CAR-treated surviving mice were tumor-free at the end of the experiment, as can be seen by histology examination using H&E staining. The SW1 mouse that survived exhibited tumors in the liver, lung and bone (FIG. 7).

Example 4. In Vivo Efficacy of Dual CAR

In the experiment performed in similar conditions as described Example 3, in order to facilitate the monitoring of the CAG tumor/tumor volume, we used a CAG-LUC cell line, which emits bio-luminescence when encounter luciferin which is injected to mice before the imaging. By that, we compared the tumor intensity in each mouse, and followed the efficacy of the treatment in each group. The results are presented in FIG. 8

Figure 8:
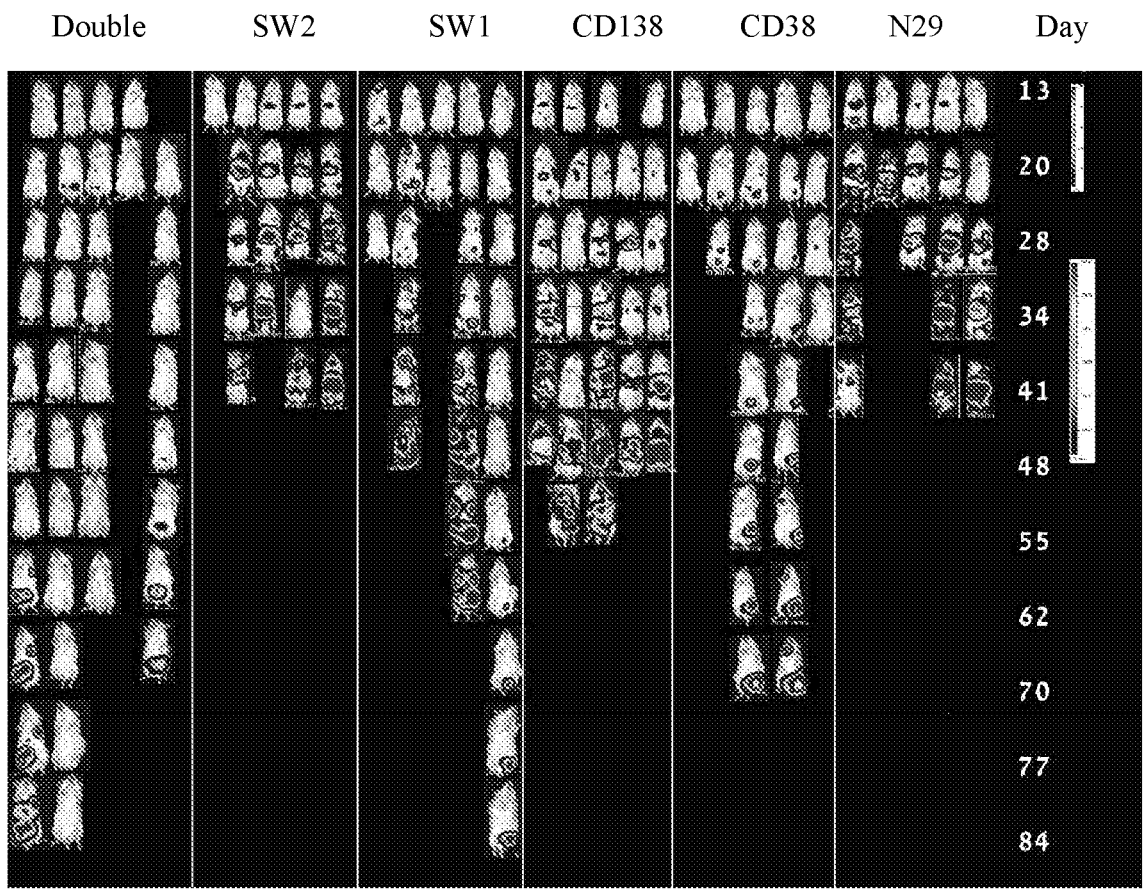
FIG. 8 shows the images of the luciferase-expressing MM tumor (CAG-Luc) in treated mice. Mice injected with MM CAG-Luc following by injection of different CARs (day 8) were monitored for the therapeutic effect.

It can be seen from FIG. 8 that all mice treated with αCD38 or Dual-CAR T-cells and most of the mice treated by switch 1 (corresponding to SW1) were tumor free on day 13. On the contrary, mice treated with switch 2 (corresponding to SW2), CD138, and N29 CAR T-cells developed tumor already on day 13. Contrary to mice treated with SW1 and αCD38 CARs, mice treated with Dual CAR remained cancer free until day 48, and 60% of them remained cancer free until day 62. Most of the mice in other groups were sacrificed before day 55 as for tumor burden and loss of weight. It is clear that treatment with dual-CAR T-cells was much more efficient than any other treatment.

It can be also seen that treatment with switch 2, αCD138 or N29 CAR-T cells provided similar results characterized by fast development of the tumor. Treatment with switch 1 was, in average, less efficient than treatment with αCD38 indicating that separation of a costimulatory domain and activation domain affects the efficacy of activation of the modified T-cell and may improve the "off-target" effect.

Figure 9:
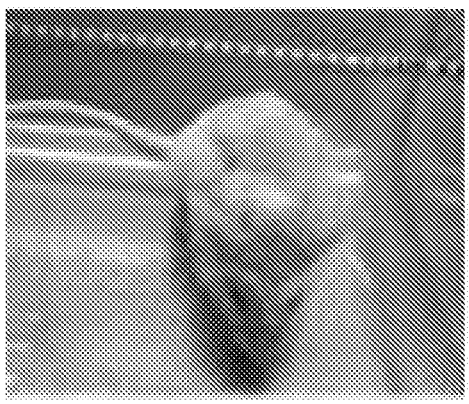
FIG. 9 shows the toxicity of CD138 CAR T-cells to mice skin (left panel mice—treated with CAR-CD38 T-cells), in contrast to the absence of this side effect when treated with Dual CAR T-cells (right panel).
Figure 9:
Figure 9:
Figure 9:

The mice were followed for their condition as well. As can be seen from FIG. 9, mice that received the CAR 138 showed skin irritation as for cross reactivity between CD138 mouse and human antigen that is expressed on their skin. These side effects were not present when the mice were treated with Dual CAR T-cells. This provides an additional proof that of T-cells carrying Dual CAR were not full activated in the present of only one antigen, i.e. CD138 (there is not CD38 antigen on skin cells), thus provide less side effects.

Although the present invention has been described herein above by way of preferred embodiments thereof, it can be modified, without departing from the spirit and nature of the subject invention as defined in the appended claims.

The invention claimed is:

1. A T-cell genetically modified to express at least two distinct separate chimeric antigen receptors (CARs), wherein the first CAR comprises an antigen binding domain that binds specifically to CD138 and the second CAR comprises an antigen binding domain that binds specifically to CD38, wherein one of the CARs comprises an activation domain and is devoid of a costimulatory domain and the other CAR comprises a costimulatory domain and is devoid of an activation domain.

2. The T-cell of claim 1, wherein the antigen binding domain that binds specifically to CD138 is a single chain variable fragment (anti-CD138 scFv) and the antigen binding domain that binds specifically to CD38 is a single chain variable fragment (anti-CD38 scFv).

3. The T-cell of claim 2, wherein the anti-CD138 scFv comprises a VL domain having the amino acid sequence of SEQ ID NO: 13 and a VH domain having the amino acid sequence of SEQ ID NO: 14; and/or wherein the anti-CD38 scFv domain comprises a VL domain having the amino acid sequence of SEQ ID NO: 15 and a VH domain having the amino acid sequence of SEQ ID NO: 16, wherein the VL and the VH domains are bound by a peptide linker.

4. The T-cell of claim 1, wherein:
(i) the first CAR comprises an activation domain and is devoid of a costimulatory domain and the second CAR comprises a costimulatory domain and is devoid of an activation domain; or
(ii) the first CAR comprises a costimulatory domain and is devoid of an activation domain and the second CAR comprises an activation domain and is devoid of a costimulatory domain.

5. The T-cell of claim 1, characterized by at least one of:
(i) the costimulatory domain is selected from a costimulatory domain of CD28, 4-1BB, OX40, iCOS, CD27, CD80, CD70 and the activation domain is selected from an FcRγ and CD3-ζ activation domain;
(ii) the activation domain is FcRγ activation domain having the amino acid sequence of SEQ ID NO: 23 and the costimulatory domain is a costimulatory domain of CD28 having the amino acid sequence of SEQ ID NO: 22; and
(iii) the peptide linker is a peptide having the amino acid sequence of SEQ ID NO: 17.

6. The T cell of claim 1, wherein the first CAR has the amino acid sequence of SEQ ID NO: 24, and the second CAR has the amino acid sequence of SEQ ID NO: 25.

7. The T-cell of claim 1, comprising at least one copy of one or more DNA constructs encoding the at least two distinct separate chimeric antigen receptors (CARs), wherein the first CAR comprises an anti-CD138 scFv and the second CAR comprises an anti-CD38 scFv.

8. The T-cell of claim 7, comprising either at least one copy of a DNA construct selected from the group consisting of:
(I) a DNA construct encoding for: (A) from 5' to 3', (i) a leader peptide, (ii) anti-CD138 scFv, (iii) a transmembrane domain I, (iv) a costimulatory domain or an activation domain, and (B) from 5' to 3' (v) a leader peptide, (vi) anti-CD38 scFv domain, (vii) a transmembrane domain II and (viii) an activation domain or a costimulatory domain; wherein (A) and (B) are separated by a self-cleaving peptide;
(II) a DNA construct encoding, from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-CD38 scFv domain, (viii) a transmembrane domain II and (ix) an activation domain; and
(III) a DNA construct encoding from 5' to 3', (i) a leader peptide, (ii) anti-CD38 scFv, (iii) a transmembrane domain II, (iv) an activation domain, (v) a self-cleaving peptide, (vi) a leader peptide, (vii) anti-CD138 scFv domain, (viii) a transmembrane domain I and (ix) a costimulatory domain, or two different DNA constructs, wherein the first DNA construct comprises a DNA sequence encoding, from 5' to 3', (i) a leader peptide, (ii) anti-CD138 scFv, (iii) a transmembrane domain I and (iv) a costimulatory domain or an activation domain, and the second DNA construct comprises a DNA sequence encoding from 5' to 3' (i) a leader peptide, (ii) anti-CD38 scFv domain, (iii) a transmembrane domain II and (iv) an activation domain or a costimulatory domain.

9. The T-cell of claim 8, wherein the DNA construct is characterized by at least one of:
(i) the leader peptide has the amino acid sequence of SEQ ID NO: 20;
(ii) the activation domain has the amino acid sequence of SEQ ID NO: 23;
(iii) the costimulatory domain has the amino acid sequence of SEQ ID NO: 22;
(iv) the anti-CD138 scFv domain has the amino acid sequence of SEQ ID NO: 18;
(v) the anti-CD38 scFv domain has the amino acid sequence of SEQ ID NO: 19;
(vi) the self-cleaving peptide is selected from the peptide having the amino acid sequence of SEQ ID NO: 26, IRES peptide;
(vii) the leader peptide is encoded by the DNA sequence set forth in SEQ ID NO: 39;
(viii) the anti-CD138 scFv is encoded by the DNA sequence set forth in SEQ ID NO: 28;
(ix) the anti-CD38 scFv is encoded by the DNA sequence set forth in SEQ ID NO: 29;
(x) the costimulatory domain is encoded by the DNA sequence set forth in SEQ ID NO: 30; and
(xi) the activation domain is encoded by the DNA sequence set forth in SEQ ID NO: 31.

10. The T-cell of claim 7, comprising (i) at least one copy of a DNA construct having the DNA sequence of SEQ ID NO: 34; or (ii) comprising at least one copy of a DNA construct comprising the DNA sequence of SEQ ID NO: 32 and at least one copy of a DNA construct comprising the DNA sequence of SEQ ID NO: 33.

11. The T-cell of claim 1, wherein the T cell is selected from a CD4+ T-cell and a CD8+ T-cell.

12. A pharmaceutical composition comprising a plurality of the T cell according to claim 1, and a pharmaceutically acceptable carrier.

13. A method of treating multiple myeloma in a subject in need thereof, the method comprising administering to the subject an effective amount of a plurality of the T cell according to claim 1.

14. A DNA construct encoding an amino acid sequence selected from the group consisting of:
(A) from 5' to 3', (i) a leader peptide, (ii) anti-CD138 scFv, (iii) a transmembrane domain I, (iv) a costimulatory domain or; an activation domain, (v) a self-cleaving peptide, (vi) a leader peptide, (vii) anti-CD38 scFv domain, (viii) a transmembrane domain II, and (ix) a costimulatory domain or an activation domain;
(B) from 5' to 3', (i) a leader peptide, (ii) anti-CD38 scFv domain, (iii) a transmembrane domain II, (iv) an activation domain or a costimulatory domain, (v) a self-cleaving peptide, (vi) a leader peptide, (vii) anti-CD138 scFv, (viii) a transmembrane domain I, and (ix) a costimulatory domain or an activation domain;
(C) from 5' to 3', (i) a leader peptide, (ii) anti-CD138 scFv, (iii) a transmembrane domain I, (iv) a costimulatory domain, (v) a self-cleaving peptide, (vi) a leader peptide, (vii) anti-CD38 scFv domain, (viii) a transmembrane domain II, and (ix) an activation domain; and (D) from 5' to 3', (i) a leader peptide, (ii) anti-CD38 scFv, (iii) a transmembrane domain II (iv) an activation domain, (v) a self-cleaving peptide, (vi) a leader peptide, (vii) anti-CD138 scFv domain, (viii) a transmembrane domain I, and (ix) a costimulatory domain.

15. The DNA construct according to claim 14, characterized by at least one of:
   (i) the self-cleaving peptide has the amino acid sequence of SEQ ID NO: 26;
   (ii) the leader peptide has the amino acid sequence of SEQ ID NO: 20;
   (iii) the activation domain has the amino acid sequence of SEQ ID NO: 23;
   (iv) the costimulatory domain has the amino acid sequence of SEQ ID NO: 22;
   (v) the anti-CD138 scFv domain has the amino acid sequence of SEQ ID NO: 18;
   (vi) the anti-CD38 scFv domain has the amino acid sequence of SEQ ID NO: 19;
   (vii) the self-cleaving peptide is encoded by the DNA sequence of SEQ ID NO: 27;
   (viii) the leader peptide is encoded by the DNA sequence of SEQ ID NO: 39;
   (ix) the activation domain is encoded by the DNA sequence of SEQ ID NO: 31;
   (x) the costimulatory domain is encoded by the DNA sequence of SEQ ID NO: 30;
   (xi) the anti-CD138 scFv domain is encoded by the DNA sequence of SEQ ID NO: 28; and
   (xii) the anti-CD38 scFv domain is encoded by the DNA sequence of SEQ ID NO: 29.

16. The DNA construct of claim 14, comprising (i) the DNA sequence of SEQ ID NO: 32 and the DNA sequence of SEQ ID NO: 33; or (ii) the DNA sequence of SEQ ID NO: 34.

17. A cell comprising the DNA construct according to claim 16.

18. The cell of claim 17, wherein the cell is a T-cell, optionally wherein the T-cell is selected from a CD4+ T-cell and a CD8+ T-cell.

19. A method for preparation of T-cells genetically modified to express at least two distinct separate chimeric antigen receptors (CARs), wherein the first CAR comprises anti-CD138 scFv and the second CAR comprises anti-CD38 scFv, said method comprises transfecting T-cells with a DNA construct according to claim 14.

* * * * *